(12) United States Patent
Allen et al.

(10) Patent No.: US 9,187,712 B2
(45) Date of Patent: Nov. 17, 2015

(54) ALKOXYLATED FATTY ESTERS AND DERIVATIVES FROM NATURAL OIL METATHESIS

(75) Inventors: Dave R. Allen, Chicago, IL (US); Marcos Alonso, Chicago, IL (US); Randal J. Bernhardt, Antioch, IL (US); Aaron Brown, Chicago, IL (US); Kelly Buchek, Hoffman Estates, IL (US); Sangeeta Ganguly-Mink, Chicago, IL (US); Brian Holland, Deerfield, IL (US); Andrew D. Malec, Chicago, IL (US); Ronald A. Masters, Glenview, IL (US); Dennis S. Murphy, Libertyville, IL (US); Patti Skelton, Winder, GA (US); Brian Sook, Lawrenceville, GA (US); Michael Wiester, Chicago, IL (US); Patrick Shane Wolfe, Palatine, IL (US)

(73) Assignee: Stepan Company, Northfield, IL (US)

( * ) Notice: Subject to any disclaimer, the term of this patent is extended or adjusted under 35 U.S.C. 154(b) by 92 days.

(21) Appl. No.: 13/878,972

(22) PCT Filed: Oct. 25, 2011

(86) PCT No.: PCT/US2011/057595
§ 371 (c)(1),
(2), (4) Date: May 15, 2013

(87) PCT Pub. No.: WO2012/061092
PCT Pub. Date: May 10, 2012

(65) Prior Publication Data
US 2014/0005423 A1 Jan. 2, 2014

Related U.S. Application Data

(60) Provisional application No. 61/406,556, filed on Oct. 25, 2010, provisional application No. 61/406,570, filed on Oct. 25, 2010, provisional application No. 61/406,547, filed on Oct. 25, 2010.

(51) Int. Cl.
C11C 3/08 (2006.01)
C07C 67/26 (2006.01)
C07C 41/03 (2006.01)
(Continued)

(52) U.S. Cl.
CPC . *C11C 3/08* (2013.01); *A01N 25/02* (2013.01); *A01N 25/04* (2013.01); *A01N 25/30* (2013.01); *A01N 33/12* (2013.01); *A01N 37/18* (2013.01); *A01N 37/44* (2013.01); *A01N 41/04* (2013.01); *A61K 8/416* (2013.01); *A61K 8/42* (2013.01); *A61K 8/44* (2013.01); *A61K 8/466* (2013.01); *A61K 8/92* (2013.01); *A61Q 5/12* (2013.01); *A61Q 19/10* (2013.01); *A62D 1/0071* (2013.01); *B01F 17/0028* (2013.01); *B01F 17/0057* (2013.01); *C07C 6/04* (2013.01); *C07C 41/03* (2013.01); *C07C 43/11* (2013.01); *C07C 67/26* (2013.01); *C07C 69/533* (2013.01); *C07C 69/593* (2013.01); *C07C 209/12* (2013.01); *C07C 211/21* (2013.01); *C07C 219/08* (2013.01); *C07C 231/12* (2013.01); *C07C 237/16* (2013.01); *C07C 303/18* (2013.01); *C08G 65/2615* (2013.01); *C08K 5/01* (2013.01); *C08K 5/20* (2013.01); *C11C 3/00* (2013.01); *C11D 1/002* (2013.01); *C11D 1/04* (2013.01); *C11D 1/28* (2013.01); *C11D 1/62* (2013.01); *C11D 1/74* (2013.01); *C11D 1/83* (2013.01); *C11D 1/92* (2013.01); *C11D 1/94* (2013.01); *C11D 3/48* (2013.01); *C09K 8/00* (2013.01); *C09K 15/28* (2013.01); *C11D 1/652* (2013.01); *C11D 1/90* (2013.01)

(58) Field of Classification Search
None
See application file for complete search history.

(56) References Cited

U.S. PATENT DOCUMENTS 2,653,970 A 9/1953 Fessler et al.
3,169,142 A * 2/1965 Knaggs et al. .................. 558/33
(Continued)

FOREIGN PATENT DOCUMENTS

DE 19755559 A1 6/1999
EP 2446743 A1 5/2012
(Continued)

OTHER PUBLICATIONS

Arai, K, et al., JP10-017898, High Concentration Water-based liquid of surfactant and method for decreasing viscosity of high-concentration water-base surfactatn liquid, 1998, English translation, (7 pages).*

(Continued)

*Primary Examiner* — Yate K Cutliff
(74) *Attorney, Agent, or Firm* — Dilworth IP LLC

(57) ABSTRACT

Alkoxylated fatty ester compositions are disclosed. In one aspect, the compositions comprise a reaction product of a metathesis-derived $C_{10}$-$C_{17}$ monounsaturated acid, octadecene-1,18-dioic acid, or their ester derivatives with one or more alkylene oxides in the presence of an insertion catalyst to give an alkoxylated fatty ester. In another aspect, the metathesis-derived $C_{10}$-$C_{17}$ monounsaturated acid, octadecene-1,18-dioic acid, or its ester derivative is reacted with a glycol ether or a glycol ether alkoxylate, to give an alkoxylated fatty ester. In yet another aspect, the metathesis-derived $C_{10}$-$C_{17}$ monounsaturated acid or octadecene-1,18-dioic acid is reacted with one or more alkylene oxides to give a fatty acid alkoxylate, followed by etherification of the fatty acid alkoxylate.

5 Claims, No Drawings

(51) Int. Cl.

| | | |
|---|---|---|
| C07C 43/11 | (2006.01) | |
| C07C 6/04 | (2006.01) | |
| C07C 69/533 | (2006.01) | |
| C07C 69/593 | (2006.01) | |
| C11D 1/28 | (2006.01) | |
| C11D 1/74 | (2006.01) | |
| B01F 17/00 | (2006.01) | |
| C11D 1/83 | (2006.01) | |
| C11D 1/94 | (2006.01) | |
| C07C 211/21 | (2006.01) | |
| C07C 237/16 | (2006.01) | |
| A01N 25/04 | (2006.01) | |
| A01N 33/12 | (2006.01) | |
| A01N 37/18 | (2006.01) | |
| A01N 37/44 | (2006.01) | |
| A01N 41/04 | (2006.01) | |
| A61K 8/41 | (2006.01) | |
| A61K 8/42 | (2006.01) | |
| A61K 8/44 | (2006.01) | |
| A61K 8/46 | (2006.01) | |
| A61Q 5/12 | (2006.01) | |
| A61Q 19/10 | (2006.01) | |
| A62D 1/02 | (2006.01) | |
| C11D 1/62 | (2006.01) | |
| C11D 1/92 | (2006.01) | |
| C11D 1/04 | (2006.01) | |
| A01N 25/02 | (2006.01) | |
| A61K 8/92 | (2006.01) | |
| C08K 5/01 | (2006.01) | |
| C08K 5/20 | (2006.01) | |
| C11C 3/00 | (2006.01) | |
| C11D 3/48 | (2006.01) | |
| C07C 219/08 | (2006.01) | |
| A01N 25/30 | (2006.01) | |
| C07C 209/12 | (2006.01) | |
| C07C 231/12 | (2006.01) | |
| C07C 303/18 | (2006.01) | |
| C11D 1/00 | (2006.01) | |
| C08G 65/26 | (2006.01) | |
| C09K 8/00 | (2006.01) | |
| C09K 15/28 | (2006.01) | |
| C11D 1/90 | (2006.01) | |
| C11D 1/65 | (2006.01) | |

(56) References Cited

U.S. PATENT DOCUMENTS

| | | | |
|---|---|---|---|
| 3,544,613 A | 12/1970 | Knaggs et al. | |
| 4,087,457 A * | 5/1978 | Convers et al. | 562/122 |
| 4,148,821 A | 4/1979 | Nussbaum et al. | |
| 4,275,013 A * | 6/1981 | Tokosh et al. | 562/122 |
| 4,545,941 A * | 10/1985 | Rosenburg | 554/163 |
| 5,386,045 A * | 1/1995 | Weerasooriya et al. | 554/149 |
| 5,482,908 A | 1/1996 | Le-khac | |
| 5,753,606 A | 5/1998 | Hees et al. | |
| 5,817,844 A * | 10/1998 | Hama et al. | 554/149 |
| 6,068,849 A * | 5/2000 | Mueninghoff et al. | 424/405 |
| 6,071,873 A | 6/2000 | Mertens | |
| 6,103,770 A | 8/2000 | Trouve | |
| 6,184,400 B1 | 2/2001 | Hama et al. | |
| 6,303,564 B1 | 10/2001 | Littau et al. | |
| 6,319,887 B1 | 11/2001 | Mertens | |
| 6,395,694 B1 * | 5/2002 | Littau | 510/276 |
| 6,429,324 B1 | 8/2002 | Raths et al. | |
| 6,504,061 B1 * | 1/2003 | Okamoto et al. | 568/618 |
| 7,098,175 B2 * | 8/2006 | Hsu et al. | 510/353 |
| 7,205,268 B2 | 4/2007 | Hsu et al. | |
| 7,270,131 B2 * | 9/2007 | Hocking et al. | 134/25.2 |
| 7,291,582 B2 | 11/2007 | Hsu et al. | |
| 7,576,227 B2 | 8/2009 | Bicerano et al. | |
| 7,635,393 B2 | 12/2009 | Hsu | |
| 7,960,599 B2 | 6/2011 | Millis et al. | |
| 8,067,610 B2 | 11/2011 | Schrodi | |
| 2007/0032382 A1 * | 2/2007 | Volgas et al. | 504/101 |
| 2007/0118916 A1 | 5/2007 | Puzio et al. | |
| 2007/0187301 A1 | 8/2007 | Tran et al. | |
| 2008/0033026 A1 | 2/2008 | Zullo et al. | |
| 2008/0175930 A1 | 7/2008 | Baseeth | |
| 2009/0031614 A1 | 2/2009 | MacPherson et al. | |
| 2009/0264672 A1 * | 10/2009 | Abraham et al. | 560/190 |
| 2010/0145086 A1 | 6/2010 | Schrodi et al. | |
| 2010/0282467 A1 | 11/2010 | Hutchison et al. | |
| 2011/0113679 A1 | 5/2011 | Cohen et al. | |
| 2011/0313180 A1 | 12/2011 | Uptain et al. | |
| 2012/0071676 A1 | 3/2012 | Schrodi et al. | |
| 2012/0197031 A1 | 8/2012 | Firth et al. | |
| 2013/0035502 A1 | 2/2013 | Cohen et al. | |
| 2013/0035532 A1 | 2/2013 | Schrodi | |

FOREIGN PATENT DOCUMENTS

| | | | |
|---|---|---|---|
| JP | 05202381 | 8/1993 | |
| JP | 05202382 | 8/1993 | |
| JP | 08-269485 | * 10/1996 | C11D 1/83 |
| JP | 10-017898 | * 1/1998 | C11D 17/00 |
| WO | 9304030 | 3/1993 | |
| WO | WO-2008048522 | 4/2008 | |
| WO | 2012061103 A2 | 5/2012 | |

OTHER PUBLICATIONS

Egawa, N. et al., JP 08-269485, Concentrated liquid detergent composition, 1996, English translation, (11 pages).*
Cohen, L., et al., Identificatin of the products from the sulfonation of an oleic acid methyl ester, 2008, Tenside, Surfactants, Detergents, vol. 45, No. 4, pp. 178-181 (5 pages attached).*
Tetrahedron 68 2012, 1117.
Appl. Catal.A. 346 2009, 158.
J.C. Mol., Topics in Catalysis 27 2004, 97.
J. C. Mol., Green Chem., 4 2002, 5.
XP002736898; Cohen, L. et al. "Identification of the products from the sulfonation of an oleic acid methyl ester", Tenside, Surfactants, Detergents, 45(4), 2008, 178-181 (abstract).
Supplemental European Search Report mailed in EP 11838497.3 on Mar. 23, 2015.

* cited by examiner

ALKOXYLATED FATTY ESTERS AND DERIVATIVES FROM NATURAL OIL METATHESIS

FIELD OF THE INVENTION

The invention relates to alkoxylated fatty esters and derivatives that originate from renewable resources, particularly natural oils and their metathesis products.

BACKGROUND OF THE INVENTION

Alkoxylated fatty esters are normally manufactured by inserting of one or more alkylene oxide units, usually ethylene oxide (EO), between the oxygen and $CH_3$ portions of a methoxy group of a methyl ester using mixed oxide catalysts, typically magnesium-containing oxides (see, e.g., U.S. Pat. Nos. 5,817,844, 6,184,400, and 6,504,061). They can also be made by esterifying fatty acids (or transesterifying fatty esters of lower alcohols) with alkoxylated alcohols. In yet another method, the alkoxylated fatty esters can be made by alkoxylating fatty acids with alkylene oxides, followed by etherification of the terminal hydroxyl group.

The performance characteristics of alkoxylated fatty esters will depend on the nature of the starting fatty methyl ester or fatty acid and the proportion, kind, and distribution of oxyalkylene groups. Alkoxylated fatty esters are valuable as nonionic surfactants and as additives for a wide variety of end-use applications, including, for example agricultural uses (see U.S. Pat. No. 6,068,849 and U.S. Pat. Appl. Publ. Nos. 2007/0032382 and 2008/0175930), hard surface cleaners (U.S. Pat. Nos. 7,270,131 and 5,386,045), laundry detergent boosters (U.S. Pat. No. 7,098,175), and other detergent applications (U.S. Pat. Nos. 6,303,564, 6,395,694, and 5,753,606).

The fatty acids or esters used to make alkoxylated fatty esters and derivatives are usually made by hydrolysis or transesterification of triglycerides, which are typically animal or vegetable fats. Consequently, the fatty portion of the acid or ester will typically have 6-22 carbons with a mixture of saturated and internally unsaturated chains. Depending on source, the fatty acid or ester often has a preponderance of $C_{16}$ to $C_{22}$ component. For instance, methanolysis of soybean oil provides the saturated methyl esters of palmitic ($C_{16}$) and stearic ($C_{18}$) acids and the unsaturated methyl esters of oleic ($C_{18}$ mono-unsaturated), linoleic ($C_{18}$ di-unsaturated), and α-linolenic ($C_{18}$ tri-unsaturated) acids. The unsaturation in these acids has either exclusively or predominantly cis-configuration.

Recent improvements in metathesis catalysts (see J. C. Mol, Green Chem. 4 (2002) 5) provide an opportunity to generate reduced chain length, monounsaturated feedstocks, which are valuable for making detergents and surfactants, from $C_{16}$ to $C_{22}$-rich natural oils such as soybean oil or palm oil. Soybean oil and palm oil can be more economical than, for example, coconut oil, which is a traditional starting material for making detergents. As Professor Mol explains, metathesis relies on conversion of olefins into new products by rupture and reformation of carbon-carbon double bonds mediated by transition metal carbene complexes. Self-metathesis of an unsaturated fatty ester can provide an equilibrium mixture of starting material, an internally unsaturated hydrocarbon, and an unsaturated diester. For instance, methyl oleate (methyl cis-9-octadecenoate) is partially converted to 9-octadecene and dimethyl 9-octadecene-1,18-dioate, with both products consisting predominantly of the trans-isomer. Metathesis effectively isomerizes the cis-double bond of methyl oleate to give an equilibrium mixture of cis- and trans-isomers in both the "unconverted" starting material and the metathesis products, with the trans-isomers predominating.

Cross-metathesis of unsaturated fatty esters with olefins generates new olefins and new unsaturated esters that can have reduced chain length and that may be difficult to make otherwise. For instance, cross-metathesis of methyl oleate and 3-hexene provides 3-dodecene and methyl 9-dodecenoate (see also U.S. Pat. No. 4,545,941). Terminal olefins are particularly desirable synthetic targets, and Elevance Renewable Sciences, Inc. recently described an improved way to prepare them by cross-metathesis of an internal olefin and an α-olefin in the presence of a ruthenium alkylidene catalyst (see U.S. Pat. Appl. Publ. No. 2010/0145086). A variety of cross-metathesis reactions involving an α-olefin and an unsaturated fatty ester (as the internal olefin source) are described. Thus, for example, reaction of soybean oil with propylene followed by hydrolysis gives, among other things, 1-decene, 2-undecenes, 9-decenoic acid, and 9-undecenoic acid. Despite the availability (from cross-metathesis of natural oils and olefins) of unsaturated fatty esters having reduced chain length and/or predominantly trans-configuration of the unsaturation, alkoxylated fatty esters and their derivatives made from these feedstocks appear to be unknown. Moreover, alkoxylated fatty esters and their derivatives have not been made from the $C_{18}$ unsaturated diesters that can be made readily by self-metathesis of a natural oil.

In sum, traditional sources of fatty acids and esters used for making alkoxylated fatty esters and their derivatives generally have predominantly (or exclusively) cis-isomers and lack relatively short-chain (e.g., $C_{10}$ or $C_{12}$) unsaturated fatty portions. Metathesis chemistry provides an opportunity to generate precursors having shorter chains and mostly trans-isomers, which could impart improved performance when the precursors are converted to downstream compositions (e.g., in surfactants). New $C_{18}$ difunctional alkoxylated fatty esters and derivatives are also potentially available from oil or $C_{10}$ unsaturated acid or ester self-metathesis. In addition to an expanded variety of precursors, the unsaturation present in the precursors allows for further functionalization, e.g., by sulfonation or sulfitation.

SUMMARY OF THE INVENTION

The invention relates to alkoxylated fatty ester compositions. In one aspect, the compositions comprise a reaction product of a metathesis-derived $C_{10}$-$C_{17}$ monounsaturated acid, octadecene-1,18-dioic acid, or their ester derivatives with one or more alkylene oxides in the presence of an insertion catalyst to give an alkoxylated fatty ester. In another aspect, the metathesis-derived $C_{10}$-$C_{17}$ monounsaturated acid, octadecene-1,18-dioic acid, or its ester derivative is reacted with a glycol ether or a glycol ether alkoxylate, optionally in the presence of an esterification or transesterification catalyst, to give an alkoxylated fatty ester. In yet another aspect, the metathesis-derived $C_{10}$-$C_{17}$ monounsaturated acid or octadecene-1,18-dioic acid is reacted with one or more alkylene oxides to give a fatty acid alkoxylate, followed by etherification of the fatty acid alkoxylate. The invention includes derivatives made by sulfonating or sulfitating the alkoxylated fatty esters. Alkoxylated fatty esters and their derivatives are valuable for a wide variety of end uses, including cleaners, fabric treatment, hair conditioning, personal care (liquid cleansing products, conditioning bars, oral care products), antimicrobial compositions, agricultural uses, and oil field applications.

DETAILED DESCRIPTION OF THE INVENTION

The invention relates to alkoxylated fatty ester compositions made from a metathesis-derived $C_{10}$-$C_{17}$ monounsaturated acid, octadecene-1,18-dioic acid, or their ester derivatives.

The $C_{10}$-$C_{17}$ monounsaturated acid, octadecene-1,18-dioic acid, or its ester derivative used as a reactant is derived from metathesis of a natural oil. Traditionally, these materials, particularly the short-chain acids and derivatives (e.g., 9-decylenic acid or 9-dodecylenic acid) have been difficult to obtain except in lab-scale quantities at considerable expense. However, because of the recent improvements in metathesis catalysts, these acids and their ester derivatives are now available in bulk at reasonable cost. Thus, the $C_{10}$-$C_{17}$ monounsaturated acids and esters are conveniently generated by cross-metathesis of natural oils with olefins, preferably α-olefins, and particularly ethylene, propylene, 1-butene, 1-hexene, 1-octene, and the like. Self-metathesis of the natural oil or a $C_{10}$ acid or ester precursor (e.g., methyl 9-decenoate) provides the $C_{18}$ diacid or diester in optimal yield when it is the desired product.

Preferably, at least a portion of the $C_{10}$-$C_{17}$ monounsaturated acid has "$\Delta^9$" unsaturation, i.e., the carbon-carbon double bond in the $C_{10}$-$C_{17}$ acid is at the 9-position with respect to the acid carbonyl. In other words, there are preferably seven carbons between the acid carbonyl group and the olefin group at C9 and C10. For the $C_{11}$ to $C_{17}$ acids, an alkyl chain of 1 to 7 carbons, respectively is attached to C10. Preferably, the unsaturation is at least 1 mole % trans-$\Delta^9$, more preferably at least 25 mole % trans-$\Delta^9$, more preferably at least 50 mole % trans-$\Delta^9$, and even more preferably at least 80% trans-$\Delta^9$. The unsaturation may be greater than 90 mole %, greater than 95 mole %, or even 100% trans-$\Delta^9$. In contrast, naturally sourced fatty acids that have $\Delta^9$ unsaturation, e.g., oleic acid, usually have ~100% cis-isomers.

Although a high proportion of trans-geometry (particularly trans-$\Delta^9$ geometry) may be desirable in the metathesis-derived fatty esters and derivatives of the invention, the skilled person will recognize that the configuration and the exact location of the carbon-carbon double bond will depend on reaction conditions, catalyst selection, and other factors. Metathesis reactions are commonly accompanied by isomerization, which may or may not be desirable. See, for example, G. Djigoué and M. Meier, *Appl. Catal. A: General* 346 (2009) 158, especially FIG. 3. Thus, the skilled person might modify the reaction conditions to control the degree of isomerization or alter the proportion of cis- and trans-isomers generated. For instance, heating a metathesis product in the presence of an inactivated metathesis catalyst might allow the skilled person to induce double bond migration to give a lower proportion of product having trans-$\Delta^9$ geometry.

An elevated proportion of trans-isomer content (relative to the usual all-cis configuration of the natural monounsaturated acid or ester) imparts different physical properties to alkoxylated fatty esters and derivative compositions made from them, including, for example, modified physical form, melting range, compactability, and other important properties. These differences should allow formulators that use alkoxylated fatty esters and derivatives greater latitude or expanded choice as they use them in cleaners, fabric treatment, personal care, agricultural uses, and other end uses.

Suitable metathesis-derived $C_{10}$-$C_{17}$ monounsaturated acids include, for example, 9-decylenic acid (9-decenoic acid), 9-undecenoic acid, 9-dodecylenic acid (9-dodecenoic acid), 9-tridecenoic acid, 9-tetradecenoic acid, 9-pentadecenoic acid, 9-hexadecenoic acid, 9-heptadecenoic acid, and the like, and their ester derivatives.

Usually, cross-metathesis or self-metathesis of the natural oil is followed by separation of an olefin stream from a modified oil stream, typically by distilling out the more volatile olefins. The modified oil stream is then reacted with a lower alcohol, typically methanol, to give glycerin and a mixture of alkyl esters. This mixture normally includes saturated $C_6$-$C_{22}$ alkyl esters, predominantly $C_{16}$-$C_{18}$ alkyl esters, which are essentially spectators in the metathesis reaction. The rest of the product mixture depends on whether cross- or self-metathesis is used. When the natural oil is self-metathesized and then transesterified, the alkyl ester mixture will include a $C_{18}$ unsaturated diester. When the natural oil is cross-metathesized with an α-olefin and the product mixture is transesterified, the resulting alkyl ester mixture includes a $C_{10}$ unsaturated alkyl ester and one or more $C_{11}$ to $C_{17}$ unsaturated alkyl ester coproducts in addition to the glycerin by-product. The terminally unsaturated $C_{10}$ product is accompanied by different coproducts depending upon which α-olefin(s) is used as the cross-metathesis reactant. Thus, 1-butene gives a $C_{12}$ unsaturated alkyl ester, 1-hexene gives a $C_{14}$ unsaturated alkyl ester, and so on. As is demonstrated in the examples below, the $C_{10}$ unsaturated alkyl ester is readily separated from the $C_{11}$ to $C_{17}$ unsaturated alkyl ester and each is easily purified by fractional distillation. These alkyl esters are excellent starting materials for making the inventive alkoxylated fatty ester compositions.

Natural oils suitable for use as a feedstock to generate the $C_{10}$-$C_{17}$ monounsaturated acid, octadecene-1,18-dioic acid, or their ester derivatives from self-metathesis or cross-metathesis with olefins are well known. Suitable natural oils include vegetable oils, algal oils, animal fats, tall oils, derivatives of the oils, and combinations thereof. Thus, suitable natural oils include, for example, soybean oil, palm oil, rapeseed oil, coconut oil, palm kernel oil, sunflower oil, safflower oil, sesame oil, corn oil, olive oil, peanut oil, cottonseed oil, canola oil, castor oil, tallow, lard, poultry fat, fish oil, and the like. Soybean oil, palm oil, rapeseed oil, and mixtures thereof are preferred natural oils.

Genetically modified oils, e.g., high-oleate soybean oil or genetically modified algal oil, can also be used. Preferred natural oils have substantial unsaturation, as this provides a reaction site for the metathesis process for generating olefins. Particularly preferred are natural oils that have a high content of unsaturated fatty groups derived from oleic acid. Thus, particularly preferred natural oils include soybean oil, palm oil, algal oil, and rapeseed oil.

A modified natural oil, such as a partially hydrogenated vegetable oil, can be used instead of or in combination with the natural oil. When a natural oil is partially hydrogenated, the site of unsaturation can migrate to a variety of positions on the hydrocarbon backbone of the fatty ester moiety. Because of this tendency, when the modified natural oil is self-metathesized or is cross-metathesized with the olefin, the reaction products will have a different and generally broader distribution compared with the product mixture generated from an unmodified natural oil. However, the products generated from the modified natural oil are similarly converted to inventive alkoxylated fatty ester compositions.

An alternative to using a natural oil as a feedstock to generate the $C_{10}$-$C_{17}$ monounsaturated acid, octadecene-1, 18-dioic acid, or their ester derivatives from self-metathesis or cross-metathesis with olefins is a monounsaturated fatty acid obtained by the hydrolysis of a vegetable oil or animal fat, or an ester or salt of such an acid obtained by esterification of a fatty acid or carboxylate salt, or by transesterification of a natural oil with an alcohol. Also useful as starting compositions are polyunsaturated fatty esters, acids, and carboxylate salts. The salts can include an alkali metal (e.g., Li, Na, or K); an alkaline earth metal (e.g., Mg or Ca); a Group 13-15 metal (e.g., B, Al, Sn, Pb, or Sb), or a transition, lanthanide, or actinide metal. Additional suitable starting compositions are described at pp. 7-17 of PCT application WO 2008/048522, the contents of which are incorporated by reference herein.

The other reactant in the cross-metathesis reaction is an olefin. Suitable olefins are internal or α-olefins having one or more carbon-carbon double bonds. Mixtures of olefins can be used. Preferably, the olefin is a monounsaturated $C_2$-$C_{10}$ α-olefin, more preferably a monounsaturated $C_2$-$C_8$ α-olefin. Preferred olefins also include $C_4$-$C_9$ internal olefins. Thus, suitable olefins for use include, for example, ethylene, propylene, 1-butene, cis- and trans-2-butene, 1-pentene, isohexylene, 1-hexene, 3-hexene, 1-heptene, 1-octene, 1-nonene, 1-decene, and the like, and mixtures thereof.

Cross-metathesis is accomplished by reacting the natural oil and the olefin in the presence of a homogeneous or heterogeneous metathesis catalyst. The olefin is omitted when the natural oil is self-metathesized, but the same catalyst types are generally used. Suitable homogeneous metathesis catalysts include combinations of a transition metal halide or oxo-halide (e.g., $WOCl_4$ or $WCl_6$) with an alkylating cocatalyst (e.g., $Me_4Sn$). Preferred homogeneous catalysts are well-defined alkylidene (or carbene) complexes of transition metals, particularly Ru, Mo, or W. These include first and second-generation Grubbs catalysts, Grubbs-Hoveyda catalysts, and the like. Suitable alkylidene catalysts have the general structure:

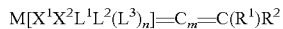

where M is a Group 8 transition metal, $L^1$, $L^2$, and $L^3$ are neutral electron donor ligands, n is 0 (such that $L^3$ may not be present) or 1, m is 0, 1, or 2, $X^1$ and $X^2$ are anionic ligands, and $R^1$ and $R^2$ are independently selected from H, hydrocarbyl, substituted hydrocarbyl, heteroatom-containing hydrocarbyl, substituted heteroatom-containing hydrocarbyl, and functional groups. Any two or more of $X^1$, $X^2$, $L^1$, $L^2$, $L^3$, $R^1$ and $R^2$ can form a cyclic group and any one of those groups can be attached to a support.

First-generation Grubbs catalysts fall into this category where m=n=0 and particular selections are made for n, $X^1$, $X^2$, $L^1$, $L^2$, $L^3$, $R^1$ and $R^2$ as described in U.S. Pat. Appl. Publ. No. 2010/0145086 ("the '086 publication"), the teachings of which related to all metathesis catalysts are incorporated herein by reference.

Second-generation Grubbs catalysts also have the general formula described above, but $L^1$ is a carbene ligand where the carbene carbon is flanked by N, O, S, or P atoms, preferably by two N atoms. Usually, the carbene ligand is party of a cyclic group. Examples of suitable second-generation Grubbs catalysts also appear in the '086 publication.

In another class of suitable alkylidene catalysts, $L^1$ is a strongly coordinating neutral electron donor as in first- and second-generation Grubbs catalysts, and $L^2$ and $L^3$ are weakly coordinating neutral electron donor ligands in the form of optionally substituted heterocyclic groups. Thus, $L^2$ and $L^3$ are pyridine, pyrimidine, pyrrole, quinoline, thiophene, or the like.

In yet another class of suitable alkylidene catalysts, a pair of substituents is used to form a bi- or tridentate ligand, such as a biphosphine, dialkoxide, or alkyldiketonate. Grubbs-Hoveyda catalysts are a subset of this type of catalyst in which $L^2$ and $R^2$ are linked. Typically, a neutral oxygen or nitrogen coordinates to the metal while also being bonded to a carbon that is α-, β-, or γ- with respect to the carbene carbon to provide the bidentate ligand. Examples of suitable Grubbs-Hoveyda catalysts appear in the '086 publication.

The structures below provide just a few illustrations of suitable catalysts that may be used:

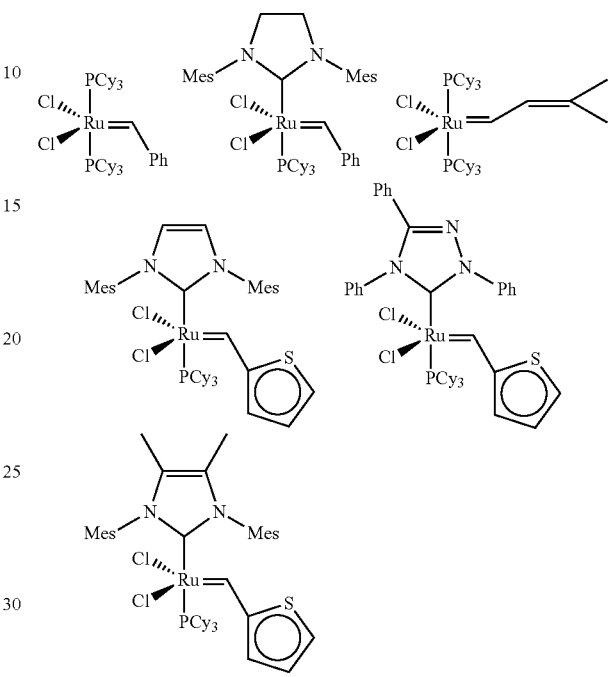

Heterogeneous catalysts suitable for use in the self- or cross-metathesis reaction include certain rhenium and molybdenum compounds as described, e.g., by J. C. Mol in Green Chem. 4 (2002) 5 at pp. 11-12. Particular examples are catalyst systems that include $Re_2O_7$ on alumina promoted by an alkylating cocatalyst such as a tetraalkyl tin lead, germanium, or silicon compound. Others include $MoCl_3$ or $MoCl_5$ on silica activated by tetraalkyltins.

For additional examples of suitable catalysts for self- or cross-metathesis, see U.S. Pat. No. 4,545,941, the teachings of which are incorporated herein by reference, and references cited therein.

In one aspect of the invention, the alkoxylated fatty ester composition comprises a product made by reacting a metathesis-derived $C_{10}$-$C_{17}$ monounsaturated acid, octadecene-1,18-dioic acid, or their ester derivatives with one or more alkylene oxides in the presence of an insertion catalyst.

The ester derivative is preferably a lower alkyl ester, especially a methyl ester. The lower alkyl esters are preferably generated by transesterifying a metathesis-derived triglyceride. For example, cross-metathesis of a natural oil with an olefin, followed by removal of unsaturated hydrocarbon metathesis products by stripping, and then transesterification of the modified oil component with a lower alkanol under basic conditions provides a mixture of unsaturated lower alkyl esters. The unsaturated lower alkyl ester mixture can be used "as is" to make the inventive fatty ester alkoxylates or it can be purified to isolate particular alkyl esters prior to making fatty ester alkoxylates.

The skilled person will appreciate that "ester derivative" here encompasses other acyl equivalents, such as acid chlorides, acid anhydrides, or the like, in addition to the lower alkyl esters discussed above.

Suitable alkylene oxides are $C_2$-$C_4$ alkylene oxides, particularly ethylene oxide, propylene oxide, and butylene oxides. Ethylene oxide and propylene oxide are preferred. Ethylene oxide is particularly preferred. Mixtures or combinations of different alkylene oxides can be used if desired to generate a random distribution or a block of alkylene oxide units.

The selection of alkylene oxide(s) and the proportion used relative to the amount of metathesis-derived acid or ester depends on the desired performance characteristics of the product and is within the skilled person's discretion. Preferably, n, which is the average number of oxyalkylene units in the alkoxylated fatty ester, is within the range of 1 to 100.

Preferably, ethylene oxide units are incorporated to enhance hydrophilicity of the composition when compared with the starting metathesis-derived acid or ester. When relatively low hydrophilicity is desired, n typically ranges from 1 to 5 EO units. For intermediate hydrophilicity, n typically ranges from 5 to 15 EO units, and for higher hydrophilicity, n typically ranges from 15 to 50 EO units.

Suitable insertion catalysts are well known. They include, for example, modified or composite metal oxides, such as magnesium oxide modified with aluminum, gallium, zirconium, lanthanum, or other transition metals, calcined hydrotalcites, calcined aluminum magnesium hydroxides, and the like. Composite oxide catalysts comprising magnesium and aluminum are preferred. Usually, the metathesis-derived fatty acid or ester is reacted in the presence of the alkylene oxide(s) and insertion catalyst and under predetermined temperature and pressure conditions, typically under nitrogen or other inert atmosphere, and the alkoxylated product is then isolated and purified by known methods. For particular examples of suitable insertion catalysts and process details for making alkoxylated fatty esters by alkylene oxide insertion, see U.S. Pat. Nos. 5,817,844, 6,184,400, and 6,504,061, the teachings of which are incorporated herein by reference. The reaction is considered complete when the product gives satisfactory analysis. For example, in the $^1$H NMR spectrum, the chemical shift of the methylene group located alpha to the carbonyl can be used to differentiate unreacted starting material from alkoxylated product.

The alkoxylated fatty esters made using the well-known alkylene oxide insertion process are unique because of the unconventional starting mixture of acid or ester derivatives produced by metathesis of natural oils.

Some inventive alkoxylated fatty esters have the formula:

$$R^2\text{—CO—O-(AO)}_n\text{—R}^1$$

wherein $R^1$ is $C_1$-$C_4$ alkyl; AO is $C_2$-$C_4$ oxyalkylene; $R^2$ is $R^3$—$C_9H_{16}$— or $R^1(AO)_n$—CO—$C_{16}H_{30}$—; $R^3$ is hydrogen or $C_1$-$C_7$ alkyl; and n, which is the average number of oxyalkylene units, has a value within the range of 1 to 100. Preferably, $R^1$ is methyl. Preferably, AO is oxyethylene, oxypropylene, or combinations thereof, more preferably oxyethylene. Preferably, $R^2$ is $R^3$—CH=CH—$(CH_2)_7$— or $R^1(AO)_nO$—CO—$(CH_2)_7$—CH=CH—$(CH_2)_7$—.

In some preferred compositions, n has a value within the range of 0.5 to 5 (also referred to herein as "low-EO" compositions). In other preferred compositions, n has a value within the range of 5 to 15 (also referred to herein as "mid-EO" compositions). In other preferred compositions, n has a value within the range of 15 to 50 (also referred to herein as "high-EO" compositions).

General Note Regarding Chemical Structures:

As the skilled person will recognize, products made in accordance with the invention are typically mixtures of cis- and trans-isomers. Except as otherwise indicated, all of the structural representations provided herein show only a trans-isomer. The skilled person will understand that this convention is used for convenience only, and that a mixture of cis- and trans-isomers is understood unless the context dictates otherwise. (The "C18-" series of products in the examples below, for instance, are nominally 100% trans-isomers whereas the "Mix-" series are nominally 80:20 trans-/cis-isomer mixtures.) Structures shown often refer to a principal product that may be accompanied by a lesser proportion of other components or positional isomers. For instance, reaction products from modified triglycerides are complex mixtures. As another example, sulfonation or sulfitation processes often give mixtures of sultones, alkanesulfonates, and alkenesulfonates, in addition to isomerized products. Thus, the structures provided represent likely or predominant products. Charges may or may not be shown but are understood, as in the case of amine oxide structures. Counterions, as in quaternized compositions, are not usually included, but they are understood by the skilled person from the context.

Some specific examples of $C_{10}$, $C_{12}$, $C_{14}$, and $C_{16}$-based alkoxylated fatty esters appear below (where n generally has a value within the range of 1 to 100):

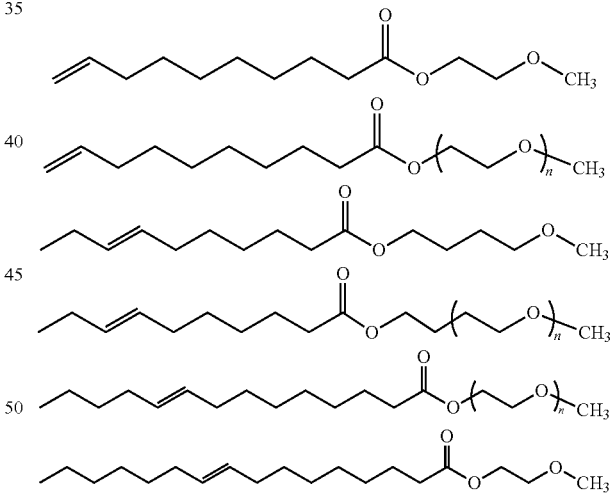

Some specific examples of $C_{18}$-based alkoxylated fatty esters (where n generally has a value within the range of 1 to 100):

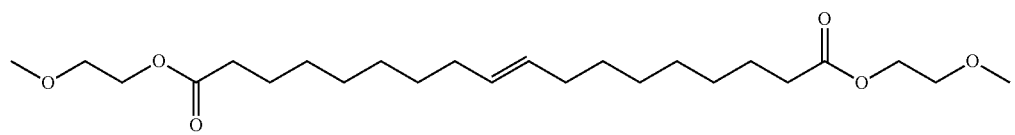

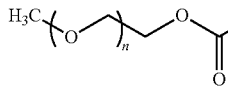 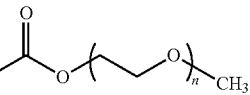

In another inventive aspect, the alkoxylated fatty ester composition comprises a reaction product of a metathesis-derived $C_{10}$-$C_{17}$ monounsaturated acid, octadecene-1,18-dioic acid, or their ester derivatives with a glycol ether or a glycol ether alkoxylate, optionally in the presence of an esterification or transesterification catalyst, to give an alkoxylated fatty ester.

Suitable glycol ethers have one terminal primary or secondary hydroxyl group and one or more ether functionalities. Glycol ethers are well known and commercially available from LyondellBasell Industries, Dow Chemical and other suppliers. They include, for example, ethylene glycol monomethyl ether, ethylene glycol monobutyl ether, diethylene glycol monomethyl ether, diethylene glycol monoethyl ether, propylene glycol monomethyl ether, propylene glycol monopropyl ether, dipropylene glycol monoethyl ether, and the like, and mixtures thereof. Particularly preferred glycol ethers are ethylene glycol monomethyl ether and diethylene glycol monomethyl ether.

Glycol ether alkoxylates are reaction products of glycol ethers and 1 to 100 equivalents per hydroxyl group of an alkylene oxide, preferably ethylene oxide, propylene oxide, or combinations thereof. Ethylene oxide (and the resulting glycol ether ethoxylates) are particularly preferred. When relatively low hydrophilicity is desired, the average number of oxyethylene units, n, typically ranges from 1 to 5 EO units. For intermediate hydrophilicity, n typically ranges from 5 to 15 EO units, and for higher hydrophilicity, n typically ranges from 15 to 50 EO units. The degree and kind of alkoxylation are readily controlled to provide the desired degree of hydrophilicity in the oxyalkylene segment. The reactants can be heated, with or without a catalyst under conditions effective to esterify or transesterify the starting acid or ester with the glycol ether or glycol ether alkoxylate. The reaction temperature is typically within the range of 80° C. to 300° C., preferably from 100° C. to 150° C., and more preferably from 110° C. to 135° C.

The relative amounts of glycol ether or glycol ether alkoxylate and ester or acid reactants used depend on the desired stoichiometry and are left to the skilled person's discretion. Typically, enough of the glycol ether or glycol ether alkoxylate is used to react with most or all of the available ester or acid groups in the other reactant. A preferred range is from 0.8 to 2.0, more preferably 0.8 to 1.2, equivalents of glycol ether or glycol ether alkoxylate per acid or ester equivalent in the $C_{10}$-$C_{17}$ monounsaturated acid, octadecene-1,18-dioic acid, or ester derivative thereof. The reaction to form the alkoxylated fatty ester can be performed under a nitrogen sparge or under vacuum to remove liberated alcohol or water. The reaction is considered complete when the product gives satisfactory analysis by $^1$H NMR spectrum or another suitable technique.

In yet another aspect, the alkoxylated fatty ester composition comprises a reaction product of a metathesis-derived $C_{10}$-$C_{17}$ monounsaturated acid or octadecene-1,18-dioic acid with one or more alkylene oxides to give a fatty acid alkoxylate, followed by etherification of the fatty acid alkoxylate. When a fatty acid is used as a reactant, the alkoxylation reaction can be uncatalyzed or catalyzed as is known in the art. Etherification of the fatty acid alkoxylate is also performed using known catalysts and processes. Usually, the terminal hydroxyl group of the fatty acid alkoxylate is reacted with an alkyl halide (e.g., methyl chloride, methyl iodide) or dialkyl sulfate (e.g., dimethyl sulfate) in the presence of a strong base (e.g., sodium, sodium hydride, potassium hydroxide).

The alkoxylated fatty esters and their derivatives have unsaturation that can be sulfonated or sulfitated if desired. Sulfonation is performed using well-known methods, including reacting the olefin with sulfur trioxide. Sulfonation may optionally be conducted using an inert solvent. Non-limiting examples of suitable solvents include liquid $SO_2$, hydrocarbons, and halogenated hydrocarbons. In one commercial approach, a falling film reactor is used to continuously sulfonate the olefin using sulfur trioxide. Other sulfonating agents can be used with or without use of a solvent (e.g., chlorosulfonic acid, fuming sulfuric acid), but sulfur trioxide is generally the most economical. The sultones that are the immediate products of reacting olefins with $SO_3$, chlorosulfonic acid, and the like may be subsequently subjected to a hydrolysis reaction with aqueous caustic to afford mixtures of alkene sulfonates and hydroxyalkane sulfonates. Suitable methods for sulfonating olefins are described in U.S. Pat. Nos. 3,169,142; 4,148,821; and U.S. Pat. Appl. Publ. No. 2010/0282467, the teachings of which are incorporated herein by reference.

Sulfitation is accomplished by combining an olefin in water (and usually a cosolvent such as isopropanol) with at least a molar equivalent of a sulfitating agent using well-known methods. Suitable sulfitating agents include, for example, sodium sulfite, sodium bisulfite, sodium metabisulfite, or the like. Optionally, a catalyst or initiator is included, such as peroxides, iron, or other free-radical initiators. Typically, the reaction mixture is conducted at 15-100° C. until the reaction is reasonably complete. Suitable methods for sulfitating olefins appear in U.S. Pat. Nos. 2,653,970; 4,087,457; 4,275,013, the teachings of which are incorporated herein by reference.

Exemplary sulfonated or sulfitated products (where n generally has a value within the range of 1 to 100):

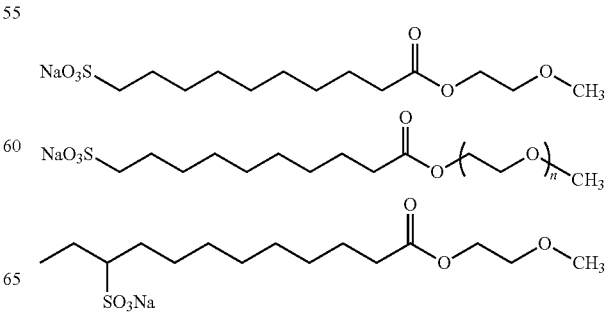

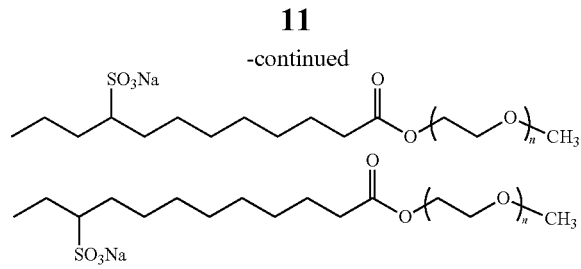

The alkoxylated fatty esters and their sulfonated or sulfitated derivatives can be incorporated into many compositions for use as, for example, surfactants, emulsifiers, skin-feel agents, film formers, rheological modifiers, biocides, biocide potentiators, solvents, release agents, and conditioners. The compositions find value in diverse end uses, such as personal care (liquid cleansing products, conditioning bars, oral care products), household products (liquid and powdered laundry detergents, liquid and sheet fabric softeners, hard and soft surface cleaners, sanitizers and disinfectants), and industrial or institutional cleaners.

The alkoxylated fatty esters and derivatives can be used in emulsion polymerizations, including processes for the manufacture of latex. They can be used as surfactants, wetting agents, dispersants, or solvents in agricultural applications, as inert ingredients in pesticides, or as adjuvants for delivery of pesticides for crop protection, home and garden, and professional applications. The alkoxylated fatty esters and derivatives can also be used in oil field applications, including oil and gas transport, production, stimulation and drilling chemicals, reservoir conformance and enhancement uses, and specialty foamers. The compositions are also valuable as foam moderators or dispersants for the manufacture of gypsum, cement wall board, concrete additives and firefighting foams. The compositions are used as coalescents for paints and coatings, and as polyurethane-based adhesives.

In food and beverage processing, the alkoxylated fatty esters and derivatives can be used to lubricate the conveyor systems used to fill containers. When combined with hydrogen peroxide, the alkoxylated fatty esters and derivatives can function as low foaming disinfectants and sanitization agents, odor reducers, and as antimicrobial agents for cleaning and protecting food or beverage processing equipment. In industrial, institutional and laundry applications, the alkoxylated fatty esters and derivatives, or their combination with hydrogen peroxide, can be used to remove soil and sanitize and disinfect fabrics and as antimicrobial film-forming compositions on hard surfaces.

The following examples merely illustrate the invention. Those skilled in the art will recognize many variations that are within the spirit of the invention and scope of the claims.

Feedstock Syntheses

Preparation of Methyl 9-Decenoate ("C10-0") and Methyl 9-Dodecenoate ("C12-0")

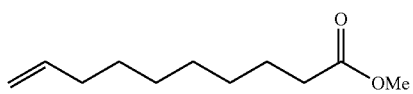

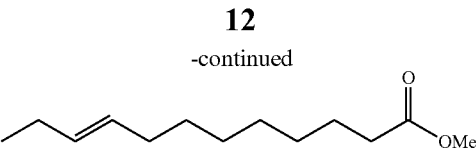

The procedures of U.S. Pat. Appl. Publ. No. 2011/0113679, the teachings of which are incorporated herein by reference, are used to generate feedstocks C10-0 and C12-0 as follows:

Example 1A

Cross-Metathesis of Soybean Oil and 1-Butene

A clean, dry, stainless-steel jacketed 5-gallon Parr reactor equipped with a dip tube, overhead stirrer, internal cooling/heating coils, temperature probe, sampling valve, and relief valve is purged with argon to 15 psig. Soybean oil (SBO, 2.5 kg, 2.9 mol, Costco, $M_n$=864.4 g/mol, 85 weight % unsaturation, sparged with argon in a 5-gal container for 1 h) is added to the Parr reactor. The reactor is sealed, and the SBO is purged with argon for 2 h while cooling to 10° C. After 2 h, the reactor is vented to 10 psig. The dip tube valve is connected to a 1-butene cylinder (Airgas, CP grade, 33 psig headspace pressure, >99 wt. %) and re-pressurized to 15 psig with 1-butene. The reactor is again vented to 10 psig to remove residual argon. The SBO is stirred at 350 rpm and 9-15° C. under 18-28 psig 1-butene until 3 mol 1-butene per SBO olefin bond are transferred into the reactor (~2.2 kg 1-butene over 4-5 h).

A toluene solution of [1,3-bis-(2,4,6-trimethylphenyl)-2-imidazolidinylidene]-dichlororuthenium(3-methyl-2-butenylidene)(tricyclohexylphosphine) (C827, Materia) is prepared in a Fischer-Porter pressure vessel by dissolving 130 mg catalyst in 30 g of toluene (10 mol ppm per mol olefin bond of SBO). The catalyst mixture is added to the reactor via the reactor dip tube by pressurizing the headspace inside the Fischer-Porter vessel with argon to 50-60 psig. The Fischer-Porter vessel and dip tube are rinsed with additional toluene (30 g). The reaction mixture is stirred for 2.0 h at 60° C. and is then allowed to cool to ambient temperature while the gases in the headspace are vented.

After the pressure is released, the reaction mixture is transferred to a round-bottom flask containing bleaching clay (Pure-Flo® B80 CG clay, product of Oil-Dri Corporation of America, 2% w/w SBO, 58 g) and a magnetic stir bar. The reaction mixture is stirred at 85° C. under argon. After 2 h, during which time any remaining 1-butene is allowed to vent, the reaction mixture cools to 40° C. and is filtered through a glass frit. An aliquot of the product mixture is transesterified with 1% w/w NaOMe in methanol at 60° C. By gas chromatography (GC), it contains: methyl 9-decenoate (22 wt. %), methyl 9-dodecenoate (16 wt. %), dimethyl 9-octadecenedioate (3 wt. %), and methyl 9-octadecenoate (3 wt. %).

The results compare favorably with calculated yields for a hypothetical equilibrium mixture: methyl 9-decenoate (23.4 wt. %), methyl 9-dodecenoate (17.9 wt/%), dimethyl 9-octadecenedioate (3.7 wt. %), and methyl 9-octadecenoate (1.8 wt. %).

Example 1B

The procedure of Example 1A is generally followed with 1.73 kg SBO and 3 mol 1-butene/SBO double bond. An aliquot of the product mixture is transesterified with sodium methoxide in methanol as described above. The products (by GC) are: methyl 9-decenoate (24 wt. %), methyl 9-dodecenoate (18 wt. %), dimethyl 9-octadecenedioate (2 wt. %), and methyl 9-octadecenoate (2 wt. %).

Example 1C

The procedure of Example 1A is generally followed with 1.75 kg SBO and 3 mol 1-butene/SBO double bond. An aliquot of the product mixture is transesterified with sodium methoxide in methanol as described above. The products (by GC) are: methyl 9-decenoate (24 wt. %), methyl 9-dodecenoate (17 wt. %), dimethyl 9-octadecenedioate (3 wt. %), and methyl 9-octadecenoate (2 wt. %).

Example 1D

The procedure of Example 1A is generally followed with 2.2 kg SBO and 3 mol 1-butene/SBO double bond. Additionally, the toluene used to transfer the catalyst (60 g) is replaced with SBO. An aliquot of the product mixture is transesterified with sodium methoxide in methanol as described above. The products (by GC) are: methyl 9-decenoate (25 wt. %), methyl 9-dodecenoate (18 wt. %), dimethyl 9-octadecenedioate (3 wt. %), and methyl 9-octadecenoate (1 wt. %).

Example 1E

Separation of Olefins from Modified Triglyceride

A 12-L round-bottom flask equipped with a magnetic stir bar, heating mantle, and temperature controller is charged with the combined reaction products from Examples 1A-1D (8.42 kg). A cooling condenser with a vacuum inlet is attached to the middle neck of the flask and a receiving flask is connected to the condenser. Volatile hydrocarbons (olefins) are removed from the reaction product by vacuum distillation. Pot temperature: 22° C.-130° C.; distillation head temperature: 19° C.-70° C.; pressure: 2000-160 μtorr. After removing the volatile hydrocarbons, 5.34 kg of non-volatile residue remains. An aliquot of the non-volatile product mixture is transesterified with sodium methoxide in methanol as described above. The products (by GC) are: methyl 9-decenoate (32 wt. %), methyl 9-dodecenoate (23 wt. %), dimethyl 9-octadecenedioate (4 wt. %), and methyl 9-octadecenoate (5 wt. %). This mixture is also called "UTG-0." (An analogous product made from palm oil is called "PUTG-0.")

Example 1F

Methanolysis of Modified Triglyceride

A 12-L round-bottom flask fitted with a magnetic stir bar, condenser, heating mantle, temperature probe, and gas adapter is charged with sodium methoxide in methanol (1% w/w, 4.0 L) and the non-volatile product mixture produced in Example 1E (5.34 kg). The resulting light-yellow heterogeneous mixture is stirred at 60° C. After 1 h, the mixture turns homogeneous and has an orange color (pH=11). After 2 h of reaction, the mixture is cooled to ambient temperature and two layers form. The organic phase is washed with aqueous methanol (50% v/v, 2×3 L), separated, and neutralized by washing with glacial acetic acid in methanol (1 mol HOAc/mol NaOMe) to pH=6.5. Yield: 5.03 kg.

Example 1G

Isolation of Methyl Ester Feedstocks

A 12-L round-bottom flask fitted with a magnetic stirrer, packed column, and temperature controller is charged with the methyl ester mixture produced in example 1F (5.03 kg), and the flask is placed in a heating mantle. The glass column is 2"×36" and contains 0.16" Pro-Pak™ stainless-steel saddles (Cannon Instrument Co.). The column is attached to a fractional distillation head to which a 1-L pre-weighed flask is fitted for collecting fractions. Distillation is performed under vacuum (100-120 μtorr). A reflux ratio of 1:3 is used to isolate methyl 9-decenoate ("C10-0") and methyl 9-dodecenoate ("C12-0"). Samples collected during the distillation, distillation conditions, and the composition of the fractions (by GC) are shown in Table 1. A reflux ratio of 1:3 refers to 1 drop collected for every 3 drops sent back to the distillation column. Combining appropriate fractions yields methyl 9-decenoate (1.46 kg, 99.7% pure) and methyl 9-dodecenoate (0.55 kg, >98% pure).

TABLE 1

Isolation of C10-0 and C12-0 by Distillation

| Distillation Fractions # | Head temp. (° C.) | Pot temp. (° C.) | Vacuum (μtorr) | Weight (g) | C10-0 (wt %) | C12-0 (wt %) |
|---|---|---|---|---|---|---|
| 1 | 40-47 | 104-106 | 110 | 6.8 | 80 | 0 |
| 2 | 45-46 | 106 | 110 | 32.4 | 99 | 0 |
| 3 | 47-48 | 105-110 | 120 | 223.6 | 99 | 0 |
| 4 | 49-50 | 110-112 | 120 | 283 | 99 | 0 |
| 5 | 50 | 106 | 110 | 555 | 99 | 0 |
| 6 | 50 | 108 | 110 | 264 | 99 | 0 |
| 7 | 50 | 112 | 110 | 171 | 99 | 0 |
| 8 | 51 | 114 | 110 | 76 | 97 | 1 |
| 9 | 65-70 | 126-128 | 110 | 87 | 47 | 23 |
| 10 | 74 | 130-131 | 110 | 64 | 0 | 75 |
| 11 | 75 | 133 | 110 | 52.3 | 0 | 74 |
| 12 | 76 | 135-136 | 110 | 38 | 0 | 79 |
| 13 | 76 | 136-138 | 100 | 52.4 | 0 | 90 |
| 14 | 76 | 138-139 | 100 | 25.5 | 0 | 85 |
| 15 | 76-77 | 140 | 110 | 123 | 0 | 98 |
| 16 | 78 | 140 | 100 | 426 | 0 | 100 |

Preparation of Methyl 9-Hexadecenoate ("C16-0") Feedstock

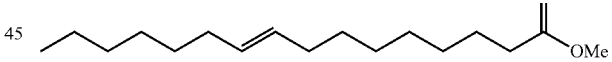

The procedures of Example 1A is generally followed except that 1-octene is cross-metathesized with soybean oil instead of 1-butene. Combined reaction products are then stripped as described in Example 1E to remove the more volatile unsaturated hydrocarbon fraction from the modified oil fraction. The procedure of Example 1F is used to convert the modified oil fraction to a methyl ester mixture that includes methyl 9-hexadecenoate. Fractional distillation at reduced pressure is used to isolate the desired product, methyl 9-hexadecenoate from other methyl esters.

Methyl Ester to Fatty Acid Conversion

Methyl esters C10-0, C12-0, C16-0, and Mix-0 are converted to their respective fatty acids C10-36, C12-39, C16-3, and Mix-67. A mixture of potassium hydroxide in glycerin (16-17 wt. %) is charged to a flask equipped with an overhead stirrer, thermocouple, and nitrogen sparge, and the solution is heated to 100° C. The methyl ester is then added. An excess of KOH (2-4 moles per mole of methyl ester) is used. For monoesters, the mole ratio is closer to 2, and for diesters it is about 4. The temperature is raised to 140° C. and heating continues until gas chromatography analysis indicates complete conversion. Deionized water is added give a weight ratio of product mixture to water of about 1.5. The solution is heated to 90° C. to melt any product that may have solidified. Aqueous sulfuric acid (30%) is added and mixed, and the layers are allowed to separate. The aqueous layer is drained. The fatty acid layer is washed with deionized water until the aqueous wash is neutral. Water content and acid value are typically measured.

Poly(Ethylene Glycol)Monomethyl Ethers

Diethylene glycol monomethyl ether (2522 g) and potassium hydroxide (21.0 g) are charged to a to a 316 stainless-steel pressure reactor. The reactor is sealed and heated to 90° C. The mixture is vacuum stripped at 90-95° C. to below 500 ppm water (by Karl Fischer titration). The reactor is purged with nitrogen prior to adding ethylene oxide (EO). Enough EO to give the desired molecular weight range is added at 145-160° C. while keeping reactor pressure below 80 psi. After EO addition is complete, the reaction mixture is held at ~150° C. for 1 h or until the pressure lines out. The product is cooled and its hydroxyl value is determined. Products prepared using this general procedure have an average of 6, 8, 11, 15, 24, or 27 moles of ethylene oxide per mole of starting glycol ether.

Fatty Acid Esterification to Make eFAME Products

C10-8: C10 Ethoxylated Fatty Acid Methyl Ester ("eFAME")

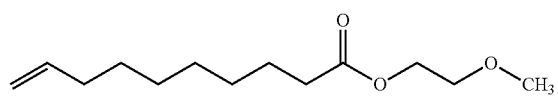 [SMILES: C=CCCCCCCCC(=O)OCCOC]

C10-36 fatty acid (196.7 g, 1.117 mol) is charged to a round-bottom flask equipped with an overhead stirrer, Dean-Stark trap, reflux condenser, thermocouple, heating mantle, and temperature controller. 2-Methoxyethanol (170.0 g) and toluene (500 mL) are added. The mixture is heated to 124° C. while p-toluenesulfonic acid (1.7 g) is added. Water of reaction begins to collect when the target temperature is reached. Heating continues for 4.5 h, and conversion to the eFAME (by $^1$H NMR) is 96%. (Signals for the hydrogens alpha to the carbonyl are used to determine degree of conversion.) The sample is stripped to remove toluene and excess 2-methoxyethanol. Residual toluene is removed by stirring at 150° C. under vacuum (1-5 mm Hg) with a low nitrogen sparge.

C10-9: C10 6EO eFAME

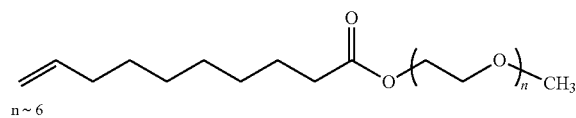

The procedure used to make C10-8 is generally followed with C10-36 fatty acid (111.2 g, 0.631 mol), polyethylene glycol monomethyl ether (188.5 g, 0.631 mol, average of about 6 EO units), toluene (500 mL), and p-toluenesulfonic acid (3.0 g). Heating continues for 10 h, and conversion to the eFAME is 96% (by gel permeation chromatography, "GPC"). Disappearance of the C10-36 fatty acid is used to measure conversion. The sample is stripped, and traces of toluene are removed by stirring at 150° C. for 3-6 h under vacuum (1-5 mm Hg) with a low nitrogen sparge.

C10-11: C10 24EO eFAME

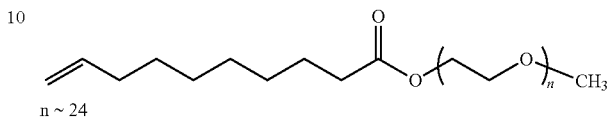

The procedure used to make C10-9 is generally followed with C10-36 fatty acid (45.0 g. 0.256 mol), polyethylene glycol monomethyl ether (267.0 g, 0.256 mol, average of about 24 EO units), toluene (500 mL), and p-toluenesulfonic acid (3.0 g). After heating 24 h, conversion (by GPC) is 97%. The product is stripped and purified as previously described.

C12-8: C10 eFAME

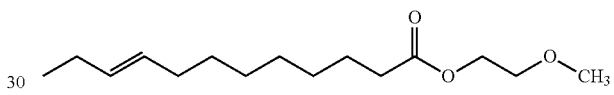

The procedure used to make C10-8 is generally followed using C12-39 fatty acid (208.0 g, 1.022 mol), 2-methoxyethanol (162.0 g), toluene (500 mL), and p-toluenesulfonic acid (1.7 g). After 3 h, conversion is 98% by $^1$H NMR. The product is stripped and purified as described earlier.

C12-9: C12 6EO eFAME

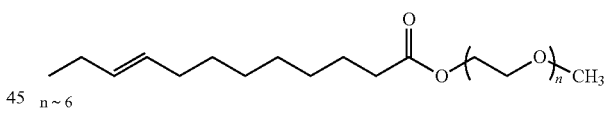

The procedure used to make C10-9 is generally followed with C12-39 fatty acid (128.5 g, 0.631 mol), polyethylene glycol monomethyl ether (191.0 g, average of about 6 EO units), toluene (500 mL), and p-toluenesulfonic acid (1.5 g). Heating continues for 12 h, and conversion to the eFAME is 94% (by GPC). The sample is stripped and purified as previously described.

C12-11: C12 27EO eFAME

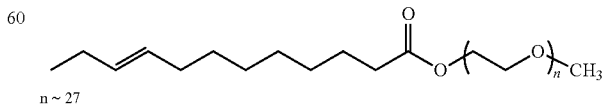

The procedure used to make C10-11 is generally followed with C12-39 fatty acid (51.9 g. 0.255 mol), polyethylene glycol monomethyl ether (297.0 g, 0.254 mol, average of about 27 EO units), toluene (500 mL), and p-toluenesulfonic acid (3.0 g, added in two portions). After heating 72 h, conversion (by GPC) is 95%. The product is stripped and purified as previously described.

C12-49: C12 15EO eFAME

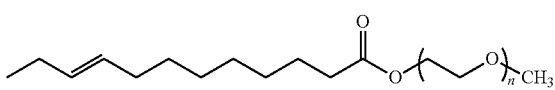

n ~ 15

The procedure used to make C10-11 is generally followed with C12-39 fatty acid (34.5 g, 0.179 mol), polyethylene glycol monomethyl ether (127.8 g, 0.182 mol, average of about 15 EO units), xylenes (500 mL), and p-toluenesulfonic acid (2.67 g, added in two portions). After heating 16 h, the catalyst is neutralized with sodium methoxide, and the reaction mixture is filtered through diatomaceous earth. The filtrate is stripped, and the product is purified as previously described.

C16-8: C16 11EO eFAME

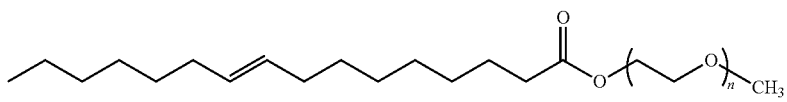

n ~ 11

The procedure used to make C10-11 is generally followed with C16-3 fatty acid (50.0 g. 0.196 mol), polyethylene glycol monomethyl ether (106.0 g, 0.199 mol, average of about 11 EO units), toluene (500 mL), and p-toluenesulfonic acid (3.0 g). After heating 7 h, the reaction is judged complete on the basis of $^1$H NMR spectroscopy. The catalyst is neutralized with sodium methoxide, and the reaction mixture is filtered through diatomaceous earth. The filtrate is stripped, and the product is purified as previously described.

Sulfitation of Olefins

C10-29: C10 eFAME Sulfonate

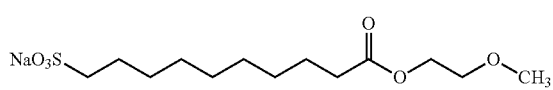

A round-bottom flask equipped with stir bar, thermocouple, heating mantle, temperature controller, and pH probe is charged with sodium bisulfite (as $Na_2S_2O_5$, 27.5 g) and deionized water (120.0 g). The pH is adjusted to 6.6 by adding sodium hydroxide (11.6 g). The mixture is heated to 75° C. Isopropyl alcohol (20.0 g) is added, followed by t-butylperoxybenzoate ("TBB," 50 μL, added by syringe). After 0.5 h, olefin C10-8 (64.3 g) is slowly added, followed by the remaining TBB (225 μL). The pH is kept at 7.0±0.1 with a low $SO_2$ sparge. After 16 h, $^1$H NMR in $D_2O$ shows olefin peaks. The pH drifts to 8.8 and is adjusted down to 6.8 with a low $SO_2$ sparge, and more isopropyl alcohol (40 mL) is added to aid with solubility. After another 5 h, pH again drifts upward and is adjusted to 6.8 with a low $SO_2$ sparge. After another 1.5 h, $^1$H NMR indicates complete reaction.

C10-10: C10 6EO eFAME Sulfonate

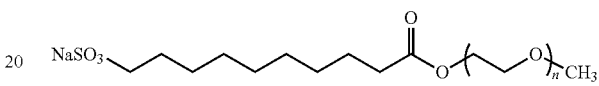

n ~ 6

The procedure used to make C10-29 is generally followed with sodium bisulfite (26.9 g, as $Na_2S_2O_5$), deionized water (240.0 g), sodium hydroxide (11.3 g), isopropyl alcohol (40.0 g), C10-9 (121.8 g, average of about 6 EO units), and t-butylperoxybenzoate (269 μL total). The pH is kept at 7.0±0.1 with a low $SO_2$ sparge. After 16 h, $^1$H NMR in $D_2O$ shows a complete reaction.

C10-30: C10 24EO eFAME Sulfonate

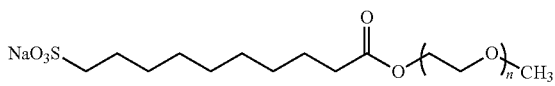

n ~ 20

The procedure used to make C10-29 is generally followed with sodium bisulfite (11.5 g, as $Na_2S_2O_5$), deionized water (290.0 g), sodium hydroxide (4.4 g), C10-11 (145.0 g, average of about 24 EO units), and t-butylperoxybenzoate (215 μL total). The pH is kept at 7.0±0.1 with a low $SO_2$ sparge. After 18 h at 75° C., $^1$H NMR in $D_2O$ shows 93% conversion.

C12-33: C12 eFAME Sulfonate

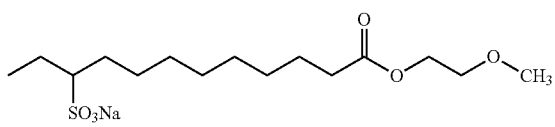

A round-bottom flask equipped with stir bar, thermocouple, heating mantle, temperature controller, and pH probe is charged with C12-8 (109.7 g) and isopropyl alcohol (110.0 g). The initial pH is 6. The contents are heated to 45° C., and t-butylperoxybenzoate (2.0 mL) is added. Separately, sodium bisulfite (as $Na_2S_2O_5$, 41.5 g) and sodium sulfite (8.0 g) are dissolved in deionized water (137.5 g). This solution is added dropwise to the olefin mixture. A precipitate forms initially, but later dissolves. The pH is adjusted to 7 by adding sodium hydroxide and the mixture stirs overnight at room temperature. $^1$H NMR indicates no reaction after three nights. The mixture is transferred to another vessel with deionized water (362.5 g, sodium sulfite (2.7 g), and TBB (2.0 mL), and the mixture is heated to 75° C. for 3 h, then cooled to room temperature and stirred for 2 days. $^1$H NMR shows 80% conversion. The mixture is reheated to 75° C. for 5 h, then cooled to room temperature and stirred overnight. No additional conversion occurs. Isopropyl alcohol is stripped and chloroform is added to isolate unreacted C12-8 (aqueous phase) from the sulfonated product, C12-33 (chloroform phase).

C12-10: C12 6EO eFAME Sulfonate

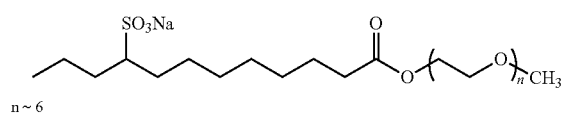

n ~ 6

The procedure used to make C12-33 is generally followed, starting with C12-9 (126.0 g, average of about 6 EO units) and isopropyl alcohol (125.0 g). After heating to 45° C., TBB (1.2 mL) is added. A solution made by dissolving sodium bisulfite (25.2 g, as $Na_2S_2O_5$) and sodium sulfite (3.3 g) in deionized water (150.0 g) is added dropwise to C12-09. The pH is held at about 7 with NaOH, and the mixture stirs overnight for 3 nights with little change by $^1$H NMR. The mixture is heated to 75° C. for 3 h, then at 45° C. with stirring for 2 days. $^1$H NMR indicates 60% conversion. TBB (1.0 mL) is added, and the mixture is heated to 75° C. for 5 h, then stirred at room temperature overnight. $^1$H NMR shows 70% conversion. Isopropyl alcohol is removed and chloroform is added to recover unreacted C12-9 (aqueous layer) and the sulfonated product, C12-10 (chloroform).

C12-32: C12 27EO eFAME Sulfonate

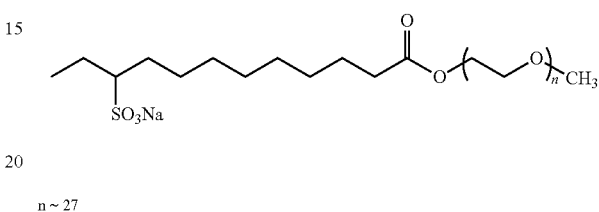

n ~ 27

The usual apparatus is charged with C12-11 (142.8 g, average of about 27 EO units), isopropyl alcohol (89.3 g), and deionized water (89.3 g). The pH is adjusted to ~7 with caustic, and TBB (1.0 g) is added. The mixture is heated to 45° C. A solution containing the sodium metabisulfite (10.2 g), sodium sulfite (2.1 g), and deionized water (142.8 g) is added dropwise. The pH is adjusted with caustic as necessary. The temperature is held at 45° C. overnight. $^1$H NMR shows no reaction. More TBB (1.0 g) is added, and the mixture is heated to 75° C. for 2 h. The pH drops to 6.8, and $^1$H NMR shows some sulfonate formation. The temperature is reduced to 45° C. and held overnight. $^1$H NMR shows ~20% conversion. More TBB (1.0 g) is added. The pH is adjusted to 6.2 via $SO_2$ gas. The mixture is heated to 75° C. and monitored. After 3 h, the pH is 5.7 and the $^1$H NMR shows 75% conversion. After 5 h, the pH is 5.0 and the $^1$H NMR shows 91% conversion. The pH is adjusted with NaOH to 6.2 each time. The mixture is heated for an additional hour, then cooled over the weekend. Isopropyl alcohol is removed via rotary evaporation. The $^1$H NMR shows 98% conversion. The mixture is diluted with DI water to give ~50% solids.

Feedstock Synthesis

Preparation of Dimethyl 9-Octadecene-1,18-dioate ("Mix-0" or "C18-0")

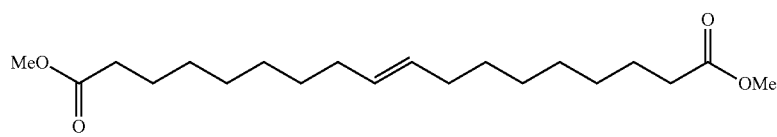 [SMILES: COC(=O)CCCCCCC/C=C/CCCCCCCC(=O)OC]

Eight samples of methyl 9-dodecenoate (10.6 g each, see Table 2) are warmed to 50° C. and degassed with argon for 30 min. A metathesis catalyst ([1,3-bis-(2,4,6-trimethylphenyl)-2-imidazolidinylidene]dichlororuthenium(3-methyl-2-butenylidene)-(tricyclohexylphosphine), product of Materia) is added to the methyl 9-dodecenoate (amount indicated in Table 2) and vacuum is applied to provide a pressure of <1 mm Hg. The reaction mixture is allowed to self-metathesize for the time reported. Analysis by gas chromatography indicates that dimethyl 9-octadecene-1,18-dioate is produced in the yields reported in Table 2. "Mix-0" is an 80:20 trans-/cis-isomer mixture obtained from the reaction mixture. Crystallization provides the all-trans-isomer feed, "C18-0."

2-Methoxyethanol (109.7 g) and toluene (250 mL) are charged to a round-bottom flask equipped with a mechanical stirrer, Dean-Stark trap, condenser, nitrogen inlet, thermocouple, heating mantle, and temperature controller. Mix-67 (195.8 g) and p-toluenesulfonic acid (1.2 g) are added. The mixture is heated to 115° C. under a light nitrogen purge and distillation proceeds. After 1 h, the reaction temperature reaches 115° C., and distillation slows. The trap is drained, and the mixture is cooled to room temperature. After standing overnight, the mixture is reheated to 120° C. and held for 6 h. Gas chromatography shows no dibasic acid present. The mixture is cooled to room temperature and is allowed to stand overnight under a light nitrogen purge. Toluene and 2-methoxyethanol are stripped by rotary evaporation and then under vacuum (1-5 mm Hg) at 150° C. with stirring and a low $N_2$ sparge. $^1$H NMR indicates complete conversion to Mix-17.

MIX-18: C18 6EO eFAME (80:20 trans-/cis-)

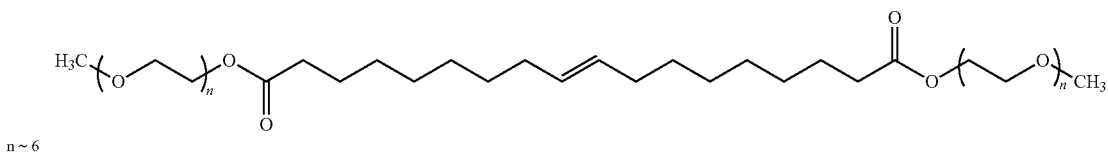

n ~ 6

TABLE 2

Self-Metathesis of Methyl 9-Dodecanoate

| Sample | Catalyst Loading (ppm mol/mol)* | Reaction Time (h) | C18-0 (GC Area %) |
|---|---|---|---|
| A | 100 | 3 | 83.5 |
| B | 50 | 3 | 82.5 |
| C | 25 | 3 | 83.0 |
| D | 10 | 3 | 66.2 |
| E | 15 | 4 | 90.0 |
| F | 13 | 4 | 89.9 |
| G | 10 | 4 | 81.1 |
| H | 5 | 4 | 50.9 |

*ppm mol catalyst/mol methyl 9-dodecenoate eFAME Products from C18 Dibasic Esters MIX-17: C18 eFAME (80:20 trans-/cis-)

The usual apparatus is charged with Mix-67 (101.0 g), poly(ethylene glycol)monomethyl ether (192.2 g, 0.644 mol, average of about 6 EO units at each end), and toluene (500 mL). p-Toluenesulfonic acid (1.5 g) is added, and the mixture is heated to reflux. After 12.5 h, $^1$H NMR indicates that the reaction is complete. The solution is cooled and neutralized with sodium methoxide (30% in MeOH, about 1 mL). Toluene is removed by rotary evaporation and then vacuum stripping (80° C., full vacuum, 3 h).

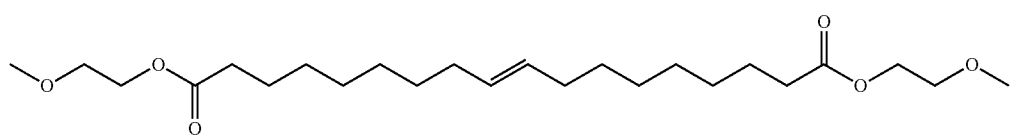

MIX-20: C18 24EO eFAME (80:20 trans-/cis-)

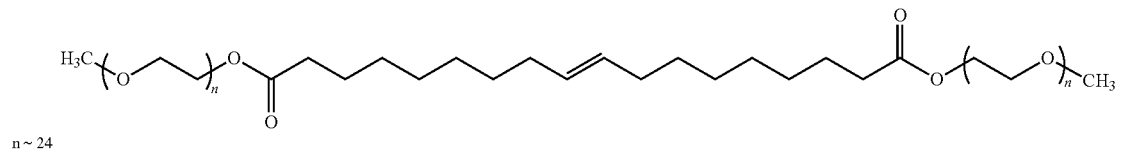

n ~ 24

The usual apparatus is charged with fatty acid Mix-67 (39.0 g, 0.124 mol), poly(ethylene glycol)monomethyl ether (259.0 g, 0.248 mol, average of about 24 EO units at each end), and toluene (500 mL). p-Toluenesulfonic acid (2.0 g) is added, and the mixture is heated to reflux. After 10 h, 1H NMR indicates >95% conversion. Toluene is removed by rotary evaporation and then vacuum stripping (150° C., 1-5 mm Hg) with a low nitrogen sparge.

MIX-61: C18 eFAME Sulfonate (80:20 trans-/cis-)

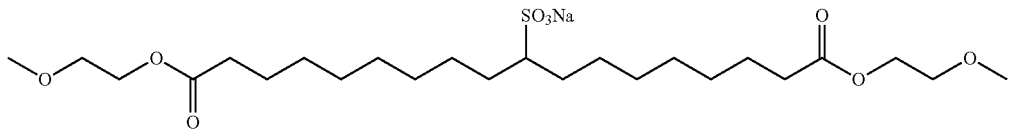

A 1-L flask equipped with overhead mechanical stirrer, thermocouple, heating mantle, and temperature controller is charged with Mix-17 (106 g) and isopropyl alcohol (300 g). t-Butylperoxybenzoate (2.0 mL) is added. Separately, sodium bisulfite (as $Na_2S_2O_5$, 17.39 g) and sodium sulfite (0.58 g) are dissolved in deionized water (300 g). This solution is added dropwise to the olefin mixture. The pH is adjusted to 6.8 by adding sodium hydroxide and the mixture stirs for 2 days at 75° C., adjusting pH after a first overnight period from about 3.8 to 6.5. The reaction mixture is stripped of isopropyl alcohol by raising the mixture temperature to 80° C. and sparging with air. The mixture separates into two layers. The top layer is unreacted olefin. This layer is collected and subjected to a second sulfitation reaction comparable to the first. The unreacted olefin collected from the second sulfitation reaction is subjected to a third sulfitation reaction. The aqueous products from all three sulfitation reactions are combined and concentrated to afford Mix-61 as an aqueous product (199 g). Moisture: 56.5%; $Na_2SO_4$: 5.0%. $^1H$ NMR analysis shows the product to be free of olefin.

Water-Soluble Herbicide Formulation Testing

Surfactant candidates for water soluble herbicide applications are examined as a replacement for the anionic, nonionic, or anionic/nonionic blend portion and compared to a known industry standard for use in paraquat, a water soluble herbicide concentrate formulation. An emulsion solubility test is conducted whereby the concentrates are diluted in water to determine if solubility is complete.

Control:

Paraquat (9.13 g of 43.8% active material) is added to a 20-mL glass vial. A known industry paraquat adjuvant (2.8 g) is added and vigorously mixed for 30 s. Deionized water (8.07 g) is added, and mixing resumes for 30 s. Standard 342 ppm water (47.5 mL) is added to a 50-mL Nessler cylinder, which is stoppered and equilibrated in a 30° C. water bath. Once the test water equilibrates, the formulated paraquat (2.5 mL) is added by pipette into the cylinder. The cylinder is stoppered and inverted ten times. Solubility is recorded as complete or incomplete. Cylinders are allowed to stand and the amount (in mL) and type of separation are recorded after 30 min., 1 h, 2 h, and 24 h. Results of the solubility testing appear in Table 3 below.

Anionic Test Sample:

Paraquat (4.57 g of 43.8% active material) is added to a 20-mL glass vial. Man eight to ten mole alkyl phenol ethoxylate surfactant (0.7 g) is added and vigorously mixed for 30 s. Test sample (0.7 g) is added and mixing resumes for 30 s. Deionized water (4.03 g) is added, and mixing resumes for 30 s. A 2.5-mL sample of the formulated paraquat is added to 47.5 mL of 342 ppm hardness water, and testing continues as described above for the control sample.

Nonionic Test Sample:

Paraquat (4.57 g of 43.8% active material) is added to a 20-mL glass vial. Test sample (0.7 g) is added and vigorously mixed for 30 s. Sodium linear alkylbenzene sulfonate ("NaLAS," 0.7 g) is added and mixing resumes for 30 s. Deionized water (4.03 g) is added, and mixing resumes for 30 s. A 2.5-mL sample of the formulated paraquat is added to 47.5 mL of 342 ppm hardness water, and testing continues as described above for the control sample.

Adjuvant (Anionic/Nonionic) Test Sample:

Paraquat (4.57 g of 43.8% active material) is added to a 20-mL glass vial. Test sample (1.4 g) is added and vigorously mixed for 30 s. Deionized water (4.03 g) is added, and mixing resumes for 30 s. A 2.5-mL sample of the formulated paraquat is added to 47.5 mL of 342 ppm hardness water, and testing continues as described above for the control sample.

Criteria for emulsion solubility: Test samples should be as good or better than the control with no separation after one hour. Four test samples perform as well as or better than the control in the emulsion stability test. Results appear in Table 3.

TABLE 3

Water Soluble Herbicide Formulation:
Emulsion stability, mL separation

| test sample | Anionic sol | 1 h | 24 h | Nonionic sol | 1 h | 24 h | Adjuvant sol | 1 h | 24 h | Rating |
|---|---|---|---|---|---|---|---|---|---|---|
| C10-30 | S | 0 | 0 | D | 0.25 | 0.25 | S | 0 | 0 | good |
| C12-10 | S | 0 | 0 | D | Tr | 0.25 | S | 0 | 0 | good |
| C12-32 | S | 0 | 0 | I | 0.5 | 0.5 | S | 0 | 0 | good |
| C12-33 | S | 0 | 0 | I | 0.25 | 0.25 | S | 0 | 0 | good |

D = dispersable;
S = soluble;
I = insoluble;
Tr = trace.
Control result:
Solubility: D;
1 h: 0 mL;
24 h: Tr.

Agricultural Products: Anionic Emulsifiers

Anionic surfactant samples contain a relatively high amount of water (>20%) and are prepared as oil-in-water (EW) concentrates. These are tested against controls containing a standard surfactant or a blank. Enough is formulated to test two water hardnesses (34 ppm and 1000 ppm) for each of the three samples.

Sample Preparation:

Pyraflufen (97.8% active, 0.30 g) is combined and with Stepan® C-25 (methyl caprylate/caprate, 7.20 g), and N-methyl-2-pyrrolidone (1.20 g), and the mixture is stirred magnetically until dissolved. In a separate container, Toximul® 8242 (castor oil ethoxylate, POE 40, product of Stepan) 0.96 g), Ninex® MT-630F (fatty acid ethoxylate, POE 30, Stepan, 0.19 g), Ninex MT-615 (fatty acid ethoxylate, POE 15, Stepan, 0.17 g), Aromatic 150 solvent (ExxonMobil, 0.37 g), and the anionic sample to be tested (0.71 g) are blended. If needed, the anionic sample is melted in an oven at 50-60° C. prior to combining with the other surfactants. When the pyraflufen has dissolved, the entire surfactant blend is added and magnetically stirred until homogeneous. Deionized water (0.90 g) is slowly added with mixing to prevent gelling. Turbidity changes are noted and recorded.

Control 1 Sample:

The same procedure is followed except that the anionic sample is replaced with Ninate® 60L (calcium alkylbenzenesulfonate, Stepan, 0.71 g).

Control 2 Sample:

No Ninate 60L (or anionic sample) is included, and the Aromatic 150 amount is increased to 1.08 g.

Emulsion Stability Testing

ASTM E1116-98 (2008) is modified as follows. Flat-bottomed, 100-mL graduated cylinders are charged with 34 ppm or 1000 ppm water (95 mL). A Mohr pipette is used to feed EW concentrate to each cylinder. Cylinders are stoppered and inverted ten times, then allowed to stand for 0.5, 1, and 24 h while recording stability at each time as type and % separation.

Spontaneity is recorded according to the following criteria: (1) poor: very thin emulsion cloud with major separation of oil droplets; (2) fair: thin emulsion cloud with minor separation of oil droplets; (3) good: thin emulsion cloud reaches the bottom of the cylinder without separation of any type; (4) excellent: thick emulsion cloud reaches the bottom of the cylinder without separation of any type.

Results are provided in Table 4. Each of the samples reported in the table is rated "good" overall as an anionic surfactant.

TABLE 4

Performance as an Anionic Emulsifier: % Separation

| | 34 ppm water | | | 1000 ppm water | | |
|---|---|---|---|---|---|---|
| | Spont. | 1 h | 24 h | Spont. | 1 h | 24 h |
| Control 1 | G | <0.2 C | 1.3 C | G | <0.2 C | 1.3 C |
| Control 2 | F | 4 C | 4.4 C | F | 4 C | 4.4 C |
| C10-30 | F | 3.8 C | 4 C | F | 2.8 C | 3 C |
| C12-10 | F+ | 4 C | 4.1 C | F+ | 3.8 C | 4 C |
| C12-32 | F+ | 3 C | 3.2 C | F+ | 2.9 C | 3.2 C |
| C12-33 | F+ | 3.2 C | 4 C | F+ | 3.9 C | 4.1 C |
| Mix-61 | F | 3.8 C | 4 C | F | 3.7 C | 3.9 C |

"C" denotes separation in the form of a cream, not a creamy oil or an oil.
"Spon." = spontaneity or bloom, rated as E (excellent), G (good), F (fair), P (poor).
Control 1 = native anionic; control 2 = no anionic emulsifier.

Agricultural Products: Nonionic Emulsifiers

Nonionic samples contain a low amount of water (<1%) and are prepared as emulsifiable concentrates (EC) with three pesticides using two different solvent systems. In the aromatic solvent series, the nonionic sample replaces Toximul® 8240 (castor oil ethoxylate, 36 POE, Stepan), and in the Hallcomid™ (N,N-dimethylcaprylamide/N,N-dimethylcapramide, Stepan) solvent series, the nonionic sample replaces Ninex® MT-630F. The amounts prepared are enough to test two water hardnesses (34 ppm and 1000 ppm) for each of the three samples.

Aromatic Solvent Series.

Sample preparation: Ninate® 60E (calcium alkylbenzenesulfonate, Stepan) and the test sample are stirred until homogeneous. If needed, the nonionic surfactant is melted in an oven at 50-60° C. prior to its combination with Ninate 60E. Controls 1-3 are made by using Toximul 8240 in the amounts indicated instead of the nonionic sample.

Formulations:

1. Bifenthrin, 240 g/L (2.99 g), Aromatic 100 (ExxonMobil, 8.05 g), Ninate 60E (0.38 g), and nonionic sample or Toximul 8240 (0.58 g).
2. 2,4-D ester, 480 g/L (8.90 g), Exxsol® D-110 (ExxonMobil, 2.50 g), Ninate 60E (0.36 g), and nonionic sample or Toximul 8240 (0.24 g).
3. Tebuconazole, 360 g/L (4.45 g), N-methyl-2-pyrrolidone (6.35 g), Ninate 60E (0.48 g), nonionic sample or Toximul 8240 (0.72 g).

Hallcomid Solvent Series.

Sample preparation: The surfactants are combined and stirred until homogeneous, with the nonionic sample melted if needed prior to combination. Controls 1-3 are made by using Ninex MT-630F in the amounts indicated instead of the nonionic sample.

Formulations:

1. Bifenthrin, 240 g/L (2.99 g), Hallcomid M-8-10 (8.29 g), Ninate 60E (0.09 g), Toximul 8320 (0.22 g), Toximul 8242 (0.29 g), and nonionic sample or Ninex MT-630F (0.13 g).
2. 2,4-D diester, 480 g/L (8.90 g), Hallcomid M-8-10 (2.38 g), Ninate 60E (0.09 g), Toximul 8320 (0.22 g), Toximul 8242 (0.29 g), and nonionic sample or Ninex MT-630F (0.13 g).
3. Tebuconazole, 360 g/L (4.45 g), Hallcomid M-8-10 (6.83 g), Ninate 60E (0.09 g), Toximul 8320 (0.22 g), Toximul 8242 (0.29 g), and nonionic sample or Ninex MT-630F (0.13 g).

Emulsion Stability Testing

ASTM E1116-98 (2008) is modified as follows. Flat-bottomed, 100-mL graduated cylinders are charged with 34 ppm or 1000 ppm water (95 mL). A Mohr pipette is used to feed EW concentrate to each cylinder. Cylinders are stoppered and inverted ten times, then allowed to stand for 0.5, 1, and 24 h while recording stability at each time as type and % separation. Spontaneity is evaluated as described for testing anionic emulsifiers.

Results with both solvent systems are provided in Tables 5A, 5B, and 6. Each sample reported in the tables is rated "good" overall as a nonionic surfactant.

TABLE 5A

Performance as a Nonionic Surfactant: Aromatic Solvents

|  |  | 34 ppm water | | | 1000 ppm water | | |
| --- | --- | --- | --- | --- | --- | --- | --- |
|  | pesticide | Spon. | 1 h | 24 h | Spon. | 1 h | 24 h |
| Control 1 | Bifenthrin | G | 2.5 C | 3 C, 1 CO, 1 O | G | 2 C | 2 C, 1 CO, 1 O |
|  | 2,4-D | F | 2.5 O | 5 O | F | 4.8 O | 5 O |
|  | Tebucon. | F | 1.6 C | 3 C, 2 OC | G | 1.8 C | 1.5 C, 2.5 OC |
| C10-8 | Bifenthrin | P | 6.5 CO | 3 C, 3 O | P | 6.5 CO | 2 C, 4 O |
|  | 2,4-D | P | 3.5 CO | 4 CO | P | 4 CO | 5 CO |
|  | Tebucon. | P | 2 C | 2 C | P | 2 C | 2 C |
| C10-9 | Bifenthrin | P | 2 O | 5 O | P | 6 O | 6 O |
|  | 2,4-D | P | 4 O | 5 O | P | 4 O | 5 O |
|  | Tebucon. | P | 2 C | 2 C | P | 2 C | 3 C |
| C10-11 | Bifenthrin | F− | 5.2 C | 5 C, 1 O | F− | 6 C | 4.5 C, 0.5 O |
|  | 2,4-D | F− | 4 C | 6 C | F− | 3 C | 4.8 C |
|  | Tebucon. | P | 2 S | 3.5 S, 0.5 C | P | 2 S | 3 S |
| C12-8 | Bifenthrin | P | 4.5 CO | 4 CO, 1 O | P | 4 CO | 4 CO, 1 O |
|  | 2,4-D | P | 3.5 O | 4 CO | P | 5 O | 5 CO |
|  | Tebucon. | P | 3 FS | 4 FS | P | 2.8 FS | 3 FS |
| C12-9 | Bifenthrin | F | 3 O, 2 C | 5 O | F | 5 O, 1 C | 5 O |
|  | 2,4-D | P | 2 O | 4 O | P | 4.8 O | 5 O |
|  | Tebucon. | P | 2 OS | 3.5 OS | P | 3 OS | 3.8 OS |
| C12-11 | Bifenthrin | F− | 5.1 C | 6.2 C | F− | 6.5 C | 6 C |
|  | 2,4-D | F− | 4.9 C | 6.5 C | F− | 4.5 C | 5 C |
|  | Tebucon. | P+ | 1.2 OS | 2 OS, 1 C | P+ | 2.1 OS | 3 CO |

Spontaneity:
G = good;
F = fair;
P = poor.
Appearance:
C = creamy;
CO = creamy oil;
O = oil;
OC = oily cream;
S = sediment;
FS = flaky sediment;
OS = oily sediment.
Numbers are amounts in mL.
Control 1 replaces test sample with Toximul 8240 (castor oil ethoxylate).

TABLE 5B

Performance as a Nonionic Surfactant: Aromatic Solvents (cont)

|  |  | 34 ppm water | | | 1000 ppm water | | |
| --- | --- | --- | --- | --- | --- | --- | --- |
|  | pesticide | Spon. | 1 h | 24 h | Spon. | 1 h | 24 h |
| Control 1 | Bifenthrin | G | 2.5 C | 3 C, 1 CO, 1 O | G | 2 C | 2 C, 1 CO, 1 O |
|  | 2,4-D | F | 2.5 O | 5 O | F | 4.8 O | 5 O |
|  | Tebucon. | F | 1.6 C | 3 C, 2 OC | G | 1.8 C | 1.5 C, 2.5 OC |
| C16-8 | Bifenthrin | G | no sep | 2.5 C | G | 5.6 CO | 6.5 CO |
|  | 2,4-D | G | 1 C | 4 C | F | 3.7 CO | 5 O |
|  | Tebucon. | P | 2 CO | 2.5 O, 2.5 CO | P | 2 C | 3 CO |
| Mix-17 | Bifenthrin | VP | 5.5 CO | 1 O, 5 CO | VP | 4.5 CO | 4 O, 1 CO |
|  | 2,4-D | VP | 6 C | 6 C | VP | 4.2 CO | 4 CO |
|  | Tebucon. | P | 2 GC | 3 GC | P | 2.1 GC | 3 GC |
| Mix-18 | Bifenthrin | P | 3.4 CO | 6.5 C | P | 5 CO | 5 O |
|  | 2,4-D | P | 6.5 CO | 8 C | P | 4 CO | 4 CO |
|  | Tebucon. | P | 2 C | 2 CO, 3 C | P | 2.2 C | 3.5 CO |

TABLE 5B-continued

Performance as a Nonionic Surfactant: Aromatic Solvents (cont)

| | | 34 ppm water | | | 1000 ppm water | | |
|---|---|---|---|---|---|---|---|
| | pesticide | Spon. | 1 h | 24 h | Spon. | 1 h | 24 h |
| Mix-20 | Bifenthrin | P | 6.8 C | 6.9 C | P | 7 C | 5.2 C |
| | 2,4-D | P | 4.5 C | 3 CO, 4 C | P | 5 C | 1 CO, 4 C |
| | Tebucon. | P | 2 O | 3 CO, 4 C | P | 2 O | 2 O, 1 FC |

Spontaneity:
G = good;
F = fair;
P = poor;
VP = very poor.
Appearance:
C = creamy;
CO = creamy oil;
O = oil;
OC = oily cream;
FC = flaky cream;
GC = gritty cream;
S = sediment;
FS = flaky sediment;
OS = oily sediment.
Numbers are amounts in mL.
Control 1 replaces test sample with Toximul 8240 (castor oil ethoxylate).

TABLE 6

Performance as a Nonionic Surfactant: Hallcomid Solvent

| | | 34 ppm water | | | 1000 ppm water | | |
|---|---|---|---|---|---|---|---|
| | pesticide | Spon. | 1 h | 24 h | Spon. | 1 h | 24 h |
| Control 2 | Bifenthrin | G | 6 OC | 6 O | G | 6 OC | 6 O |
| | 2,4-D | F | 5 C | 9.8 C | F | 5.5 C | 9.5 C |
| | Tebucon. | G | 1 C | 4 C | G | 1 C | 4 C, 4 CO |
| C10-8 | Bifenthrin | P | 15 C | 2 OC, 4 O | P | 15 C | 2 OC, 5 O |
| | 2,4-D | G | 7 C | 10 C | G | 8 C | 10 C |
| | Tebucon. | F | 3 C | 7 C | F | 3 C | 7 C |
| C10-9 | Bifenthrin | F | 10 C | 2 OC, 5 O | F | 9 C | 7 O |
| | 2,4-D | G | 7 C | 9 C | G | 7 C | 9 C |
| | Tebucon. | F | 2 C | 6 C | F | 2 C | 9 C |
| C12-8 | Bifenthrin | F | 11 C | 6 O | F | 9 CO | 6 O |
| | 2,4-D | F+ | 6 C | 8.2 C | F+ | 6 C | 7.5 C |
| | Tebucon. | G– | 2 C | 3.5 C, 2 O | G– | 2 C | 4 C, 2 O |
| C12-9 | Bifenthrin | F | 8 C | 6 O | F | 7.5 C | 6 O |
| | 2,4-D | F+ | 7 C | 8.8 C | F+ | 6 C | 8 C |
| | Tebucon. | F+ | 3 C | 5.5 CO | F+ | 2 C | 6 CO |
| Mix-17 | Bifenthrin | E | no sep | no sep | F | 11.8 C | 3 O, 3 HO |
| | 2,4-D | F | 6 C | 9.5 C | G | 6.5 C | 7.5 C |
| | Tebucon. | G | 2.5 C | 6 C | G | 2.5 C | 6 C |
| Mix-18 | Bifenthrin | G | no sep | no sep | P | 10 C | 3 O, 3 CO |
| | 2,4-D | F | 6 C | 9 C | F | 6.5 C | 8 C |
| | Tebucon. | F | 3.2 C | 2 O, 3.5 C | F | 3.9 C | 2 O, 4 C |
| Mix-20 | Bifenthrin | G | no sep | no sep | G | 5 CO | 1 O, 5 CO |
| | 2,4-D | F | 5 C | 10.5 C | F | 5.2 C | 9 C |
| | Tebucon. | F | 3 C | 2.5 C | F | 2 C | 1.2 CO |

Spontaneity:
E = excellent;
G = good;
F = fair;
P = poor.
Appearance:
C = creamy;
CO = creamy oil;
O = oil;
HO = hazy oil;
OC = oily cream;
S = sediment;
FS = flaky sediment;
OS = oily sediment.
Numbers are amounts in mL.
Control 2 replaces test sample with Ninex MT-630F (fatty acid ethoxylate).

Agrichemical Solvent Analysis: Active Solubility

Solvency strength of potential agrichemical solvents is evaluated by identifying the solubility level of four standard pesticides in the solvent by weight percent: 2,4-D acid, imidacloprid, trifluralin and tebuconazole. Testing is performed using a 4-mL vial with a pane magnetic stirrer and an accurately weighed 2 to 2.2-g sample of solvent. The active material is also accurately weighed before addition. Initial amounts of active material are approximately: 2,4-D: 0.3 g; imidacloprid: 0.02 g; trifluralin: 0.5 g; tebuconazole: 0.3 g. Solvent and pesticide active are combined, allowed to mix for 1 h at room temperature, and then inspected for the presence of undissolved active material. Additional active material is added in appropriately small increments until it no longer dissolves completely. This mixture is then stirred for 24 h at room temperature, and if the active has completely dissolved, additional active ingredient is added and the mixture is stirred another 24 h at room temperature. The percent solubility is recorded, and performance is compared with that of a standard agricultural solvent.

When the method outlined above is followed, one sample, C12-8, performs as well as the control in this test. Detailed results appear in Table 7, below:

TABLE 7

Agricultural Solvent Testing

| Solvent | 2,4-D Acid | Imidacloprid | Trifluralin | Tebuconazole |
|---|---|---|---|---|
| C12-8 | 9.2 | 0.2 | 56.7 | <0.4 |
| methyl laurate | 11.2 | 0.6 | 58.8 | 5.9 |
| $C_{12}$-$C_{14}$ dimethylamide | 38.2 | 1.9 | 64.0 | 32.2 |
| aromatic hydrocarbon | 0.6 | 1.0 | 78.9 | 4.2 |
| N-methyl-2-pyrrolidone | 39.5 | 29.3 | 78 | 62.2 |

Antimicrobial Products: Biocide Actives

Biocidal efficiency is evaluated using the rapid screen assay, an ATP-based method that measures relative kill % of bacteria in a 5-min. period. The control used is first-generation ADBAC BTC 835 (benzyldimethylammonium chloride). Test organisms: *Pseudomonas aeruginosa* and *Staphylococcus aureas*.

Twenty-four hour old test organism cultures are prepared in Mueller Hinton broth and incubated. Samples are accurately weighed in deionized water or 400 ppm water to make a 1000 ppm solution taking into account the actives level of the sample. The 24-h culture is diluted to 10 vol. % to obtain a cell concentration of $\sim 10^7$ cfu/mL (colony forming units per mL). Reagents are prepared using the instructions provided in the BacTiter-Glo™ Microbial Cell Viability Assay kit (product of Promega) and calibrated at room temperature for 15 min. Each formulation type is dispensed (90 μL at 1000 ppm) into each row of a 96-well plate. Blank medium, i.e., Mueller Hinton broth (10 μL) is dispensed in three replicate wells (1-3) to determine baseline, while the organism to be tested (10 μL) is dispensed in nine experimental replicate wells (4-12). The timer is started, and the test plate (baseline and experimental) is shaken for 30 s. At the end of an appropriate contact time (e.g. 5 min or 10 min), an equal amount of BacTiter-Glo reagent mix is added to each reaction mixture, starting with the experimental samples and ending with the baseline samples. After shaking to ensure thorough mixing, the relative luminescence units (RLUs) of each well are measured and recorded. The % kill of $10^7$ cfu/mL after 5 min. contact time for each organism in DI or hard water is calculated from:

% Kill=[1−(Ave.RLU of Wells$_{Experimental}$−Ave.RLU of Wells$_{Baseline\ Controls}$)]/80000

As shown in Table 8, four of the tested compositions perform as well as or better than the control when tested as antimicrobial actives.

TABLE 8

Performance as Antimicrobial Active % Kill at 5 min. contact time, $10^7$ cfu/mL, 1000 ppm

| | Pseudomonas aeruginosa | | Staphylococcus aureus | | Overall |
|---|---|---|---|---|---|
| | DI water | 400 ppm | DI water | 400 ppm | Rating |
| control | 29.0 | 20.1 | 48.2 | 41.7 | |
| C10-9 | 37.2 | 29.1 | 38.4 | 23.4 | good |
| C10-11 | 28.9 | 21.3 | 42.5 | 30.9 | good |
| control | 25.5 | 18.3 | 50.2 | 46.6 | |
| C12-9 | 32.6 | 23.2 | 36.2 | 3.2 | good |
| C12-11 | 34.9 | 30.1 | 42.7 | 36.2 | good | control = dimethylbenzylammonium chloride

Hard-Surface Cleaners: Aqueous Degreasers

This test measures the ability of a cleaning product to remove a greasy dirt soil from a white vinyl tile. The test is automated and uses an industry standard Gardner Straight Line Washability Apparatus. A camera and controlled lighting are used to take a live video of the cleaning process. The machine uses a sponge wetted with a known amount of test product. As the machine wipes the sponge across the soiled tile, the video records the result, from which a cleaning percentage can be determined. A total of 10 strokes are made using test formulation diluted 1:32 with water, and cleaning is calculated for each of strokes 1-10 to provide a profile of the cleaning efficiency of the product. The test sample is used as a component of different control formulations depending on whether it anionic, amphoteric, or nonionic.

Anionic Test Samples:

A neutral, dilutable all-purpose cleaner is prepared from propylene glycol n-propyl ether (4.0 g), butyl carbitol (4.0 g), sodium citrate (4.0 g), Bio-Soft® EC-690 ethoxylated alcohol (1.0 g, Stepan), test sample (0.29 g if 100% active material), and deionized water (to 100.0 g solution). The control sample for anionic testing replaces the test sample with Stepanol® WA-Extra PCK (sodium lauryl sulfate, Stepan, 1.0 g, nominally 30% active material).

Nonionic and Amphoteric Test Samples:

A neutral, dilutable all-purpose cleaner is prepared from propylene glycol n-propyl ether (4.0 g), butyl carbitol (4.0 g), sodium citrate (4.0 g), Stepanol WA-Extra PCK (sodium lauryl sulfate, 1.0 g), test sample (0.90 g if 100% active material), and deionized water (to 100.0 g solution). The control sample for nonionic/amphoteric testing replaces the test sample with Bio-Soft EC-690 (ethoxylated alcohol, 1.0 g, nominally 90% active material).

Soil Composition:

Tiles are soiled with a particulate medium (50 mg) and an oil medium (5 drops). The particulate medium is composed of (in parts by weight) hyperhumus (39), paraffin oil (1), used motor oil (1.5), Portland cement (17.7), silica 1 (8), molacca black (1.5), iron oxide (0.3), bandy black clay (18), stearic acid (2), and oleic acid (2). The oil medium is composed of kerosene (12), Stoddard solvent (12), paraffin oil (1), SAE-10 motor oil (1), Crisco® shortening, product of J.M. Smucker Co. (1), olive oil (3), linoleic acid (3), and squalene (3).

Seven nonionic (eFAME) samples and five anionic (eFAME sulfonate) samples perform as well as or better than the control in this test (see Tables 9 and 10).

TABLE 9

Control Runs for Gardner Straight Line Washability Test

| | Ave. % clean after 2, 4, 6, 8, or 10 swipes | | | | |
|---|---|---|---|---|---|
| | 2 | 4 | 6 | 8 | 10 |
| Control 1 | 52.4 | 59.0 | 62.5 | 62.8 | 63.9 |
| Control 4 | 52.5 | 58.2 | 59.5 | 60.9 | 63.3 |
| Control 5 | 50.8 | 59.2 | 63.9 | 65.3 | 67.1 |
| Control 6 | 51.2 | 57.6 | 62.7 | 62.6 | 66.0 |
| Control 8 | 49.6 | 55.9 | 56.8 | 62.8 | 64.1 |
| Control 9 | 55.5 | 61.5 | 66.0 | 65.9 | 68.4 |
| Control 16 | 50.9 | 61.5 | 63.1 | 64.0 | 67.7 |
| Control 18 | 62.2 | 67.6 | 70.4 | 71.7 | 71.7 |
| Control 21 | 64.6 | 68.8 | 70.5 | 71.2 | 72.0 |

TABLE 10

Gardner Straight-Line Washability

| | | | Ave. % clean | | | | |
|---|---|---|---|---|---|---|---|
| Sample | Con. # | Compound class | 2 | 4 | 6 | 8 | 10 | Rating |
| Nonionic Test Samples | | | | | | | | |
| C10-11 | 1 | high-EO ethoxylate | 57.7 | 64.8 | 70.2 | 70.5 | 71.9 | superior |
| C10-9 | 5 | mid-EO ethoxylate | 52.2 | 55.1 | 60.9 | 64.7 | 64.3 | equal |
| C12-9 | 8 | mid-EO ethoxylate | 48.8 | 54.8 | 59.4 | 59.8 | 61.4 | equal |
| C12-11 | 9 | high-EO ethoxylate | 62.5 | 67.2 | 70.7 | 70.1 | 69.6 | equal |
| C12-49 | 4 | high-EO ethoxylate | 53.1 | 57.3 | 59.3 | 59.4 | 61.2 | equal |
| Mix-18 | 18 | mid-EO ethoxylate | 57.8 | 61.8 | 62.3 | 63.4 | 66.2 | equal |
| Mix-20 | 18 | high-EO ethoxylate | 59.4 | 63.2 | 67.3 | 67.4 | 69.2 | equal |
| Anionic Test Samples | | | | | | | | |
| C10-10 | 16 | mid-EO ethox sulfonate | 49.9 | 57.5 | 59.7 | 61.0 | 62.6 | equal |
| C10-29 | 16 | low-EO ethox sulfonate | 54.4 | 61.6 | 63.1 | 65.6 | 67.9 | equal |
| C10-30 | 6 | high-EO ethox sulfonate | 58.8 | 63.6 | 68.3 | 68.8 | 70.6 | equal |
| C12-10 | 6 | mid-EO ethox sulfonate | 57.1 | 61.2 | 66.6 | 66.0 | 66.8 | equal |
| Mix-61 | 21 | low-EO ethox sulfonate | 58.8 | 62.5 | 64.8 | 65.0 | 65.5 | equal |

Fabric Cleaning: Booster for Bargain Laundry Detergent

This method evaluates the cleaning boosting ability of an experimental sample when used as an additive in a bargain laundry detergent formulation that contains neutralized dodecylbenzene sulfonic acid, a non-ionic surfactant such as an ethoxylated synthetic $C_{12}$-$C_{15}$ alcohol (7 EO), citric acid, monoethanolamine, triethanolamine, and a preservative. The experimental sample is tested for its ability to improve the overall cleaning performance at 1% solids level relative to Ammonyx® LO (lauramine oxide, Stepan, standard booster). Laundry detergent formula (46 g) is charged to the laundry machine, followed by soiled/stained fabric swatches that are attached to pillowcases. Wash temperature: 90° F. Rinse: 70° F. The swatches are detached from pillowcases, dried, and ironed.

Swatches are scanned to measure the L* a* b* values, which are used to calculate a soil removal index (SRI) for each type of swatch. Finally, the ΔSRI is calculated, which equals the experimental sample SRI minus the SRI of a predetermined standard laundry detergent formula (or control). When |ΔSRI|≥1, differences are perceivable to the naked eye. If the value of ΔSRI is greater than or equal to 1, the sample is superior. If ΔSRI is less than or equal to −1, the sample is inferior. If ΔSRI is greater than −1 and less than 1, the sample is considered equal to the standard.

The bargain laundry detergent with booster is prepared from sodium hydroxide-neutralized dodecylbenzene sulfonic acid (NaLAS, Bio-Soft® S-101, Stepan, 33.9% actives, 41.3 wt. %), Bio-Soft® N25-7 (fatty alcohol ethoxylate, Stepan, 5.00 wt. %), booster (either the experimental sample or Ammonyx LO, which is 30% actives, 3.33 wt. %, citric acid (50% aq. solution, 1.00 wt. %), monoethanolamine (1.00 wt. %), triethanolamine (1.00 wt. %), and deionized water plus preservative (balance to 100 wt. %).

The formulation is made by charging 90% of the total amount of water at 50° C., then adding in order, with mixing, citric acid solution, monoethanolamine, triethanolamine, neutralized sulfonic acid, Bio-Soft N25-7, and booster. The pH is adjusted to 9.5 with 25% aq. NaOH solution, and then preservative and the balance of the water are added.

The following standard soiled/stained fabric swatches are used: dust sebum on cotton (DSC); dust sebum on cotton/polyester (DSCP); beef tallow (BT); clay on cotton (CC); clay on cotton/polyester (CCP); grass on cotton (GC); red wine on cotton (RWC); blueberry on cotton (BC); coffee on cotton (COFC); cocoa on cotton (EMPA 112); blood/ink/milk on cotton (EMPA 116); and make-up on cotton (EMPA 143). At least three of each kind of swatch are used per wash. Swatches are stapled to pillowcases for laundering, and extra pillowcases are included to complete a six-pound load.

The same procedure is used to launder all of the pillowcases/swatches, with care taken to ensure that water temperature, wash time, manner of addition, etc. are held constant for the cold-water wash process. When the cycle is complete, swatches are removed from the pillowcases, dried at low heat on a rack, and pressed briefly with a dry iron.

A Hunter LabScan® XE spectrophotometer is used to determine the L* a* b* values to calculate the SRI for every type of swatch, and the stain removal index (SRI) is calculated as follows:)

$$SRI = 100 - \sqrt{(L^*_{clean} - L^*_{washed})^2 + (a^*_{clean} - a^*_{washed})^2 + (b^*_{clean} - b^*_{washed})^2}$$

$$\Delta SRI = SRI_{sample} - SRI_{standard}$$

As shown in Table 11, one tested sample (C12-33) performs as well as the control sample when evaluated as a fabric booster.

TABLE 11

Performance as a Booster for a Bargain Detergent Formulation: |ΔSRI| Values versus Ammonyx ® LO (Lauramine Oxide)

| | ΔSRI values |
|---|---|
| test sample | C12-33 |
| dust sebum on cotton (DSC) | 0.7 |
| dust sebum on cotton/polyester (DSCP) | 0.9 |
| beef tallow (BT) | −0.7 |
| clay on cotton (CC) | 0.8 |
| clay on cotton/polyester | −0.3 |
| grass on cotton (GC) | −1.6 |
| red wine on cotton (RWC) | −0.3 |
| blueberry on cotton (BC) | −0.9 |
| coffee on cotton (COFC) | −0.5 |
| cocoa on cotton (EMPA 112) | 0.5 |
| blood/ink/milk on cotton (EMPA 116) | 0.3 |
| make-up on cotton (EMPA 143) | 0.2 |
| overall rating | good |

Personal Care/Antibacterial Handsoap:
Method to Determine Foam Enhancement Benefit Foam volume, which signals "clean" to consumers, is a desirable attribute in an antibacterial handsoap. Because cationic antibacterial actives are not compatible with anionic surfactants (the best foamers), achieving sufficient foam volume with them is challenging. The method below identifies surfactants that provide more foam volume than cocamidopropylbetaine (actives/actives basis) in an antibacterial handsoap base. Formulation: deionized water (q.s. to 100 wt. %), cocoglucoside (3.0 wt. %), lauramine oxide (3.0 wt. %), benzalkonium chloride (0.1 wt. %), and test molecule or cocamidopropylbetaine (3.0 wt. %).

Solutions are prepared by combining ingredients in the order prescribed above, stirring with a stir bar or mixing gently using an overhead stirrer or manually using a spatula. Heat may be applied if the test molecule is a solid at room temperature. Mixing is maintained to ensure a homogenous solution. The pH is adjusted to 6.5+/−0.5.

Test and control solutions are compared, with and without 2% castor oil, at 0.2% total surfactant active concentration (2.22 g solution to 100 mL with tap water from Lake Michigan, ~150 ppm Ca/Mg hardness) for foam volume using the cylinder inversion test. Initial and delayed (5 min.) measurements are taken.

Rating system: Superior: a result >25 mL over the cocamidopropylbetaine control in both oil and no-oil systems. Good: a result within 25 mL of the cocamidopropylbetaine control in both oil and no-oil systems. Inferior: a result >25 mL below that of the cocamidopropylbetaine control in both oil and no-oil systems.

Compared with the controls, two test materials, C12-9 and C12-11, show good overall performance in the antibacterial handsoap tests.

The preceding examples are meant only as illustrations. The following claims define the invention.

We claim:

1. An anionic emulsifier for agricultural applications comprising:
   (a) an alkoxylated fatty ester composition comprising a reaction product of a metathesis-derived $C_{10}$-$C_{17}$ monounsaturated acid, octadecene-1,18-dioic acid, or their ester derivatives with: (a) one or more alkylene oxides in the presence of an insertion catalyst to give an alkoxylated fatty ester; (b) a glycol ether or a glycol ether alkoxylate, optionally in the presence of an esterification or transesterification catalyst, to give an alkoxylated fatty ester; or (c) one or more alkylene oxides to give a fatty acid alkoxylate, followed by etherification of the fatty acid alkoxylate;
   wherein the alkoxylated fatty ester composition has the formula:

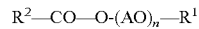
   $$R^2\text{—CO—O-(AO)}_n\text{—}R^1$$

wherein: $R^1$ is $C_1$-$C_4$ alkyl; AO is $C_2$-$C_4$ oxyalkylene; $R^2$ is $R^3$—CH=CH—$(CH_2)_7$— or $R^1(AO)_nO$—CO—$(CH_2)_7$—CH=CH—$(CH_2)_7$—; $R^3$ is hydrogen or $C_1$-$C_7$ alkyl; and n, which is the average number of oxyalkylene units, has a value within the range of 1 to 100; and
   wherein when $R^3$ is $C_1$-$C_7$ alkyl, the acid or ester derivative reactant has at least 1 mole % of trans-$\Delta^9$ unsaturation; or
   (b) a derivative made by sulfonating or sulfitating the alkoxylated fatty ester composition.

2. A nonionic emulsifier for agricultural applications comprising:
   (a) an alkoxylated fatty ester composition comprising a reaction product of a metathesis-derived $C_{10}$-$C_{17}$ monounsaturated acid, octadecene-1,18-dioic acid, or their ester derivatives with: (a) one or more alkylene oxides in the presence of an insertion catalyst to give an alkoxylated fatty ester; (b) a glycol ether or a glycol ether alkoxylate, optionally in the presence of an esterification or transesterification catalyst, to give an alkoxylated fatty ester; or (c) one or more alkylene oxides to give a fatty acid alkoxylate, followed by etherification of the fatty acid alkoxylate;
   wherein the alkoxylated fatty ester composition has the formula:

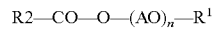
   $$R2\text{—CO—O—(AO)}_n\text{—}R^1$$

wherein: $R^1$ is $C_1$-$C_4$ alkyl; AO is $C_2$-$C_4$ oxyalkylene; $R^2$ is $R^3$—CH=CH—$(CH_2)_7$— or $R^1(AO)_nO$—CO—$(CH_2)_7$—CH=CH—$(CH_2)_7$—; $R^3$ is hydrogen or $C_1$-$C_7$ alkyl; and n, which is the average number of oxyalkylene units, has a value within the range of 1 to 100; and
   wherein when $R^3$ is $C_1$-$C_7$ alkyl, the acid or ester derivative reactant has at least 1 mole % of trans-$\Delta^9$ unsaturation; or
   (b) a derivative made by sulfonating or sulfitating the alkoxylated fatty ester composition.

3. An agricultural solvent comprising:
   (a) an alkoxylated fatty ester composition comprising a reaction product of a metathesis-derived $C_{10}$-$C_{17}$ monounsaturated acid, octadecene-1,18-dioic acid, or their ester derivatives with: (a) one or more alkylene oxides in the presence of an insertion catalyst to give an alkoxylated fatty ester; (b) a glycol ether or a glycol ether alkoxylate, optionally in the presence of an esterification or transesterification catalyst, to give an alkoxylated fatty ester; or (c) one or more alkylene oxides to give a fatty acid alkoxylate, followed by etherification of the fatty acid alkoxylate;
   wherein the alkoxylated fatty ester composition has the formula:

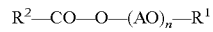
   $$R^2\text{—CO—O—(AO)}_n\text{—}R^1$$

wherein: $R^1$ is $C_1$-$C_4$ alkyl; AO is $C_2$-$C_4$ oxyalkylene; $R^2$ is $R^3$—CH=CH—$(CH_2)_7$— or $R^1(AO)_nO$—CO—$(CH_2)_7$—CH=CH—$(CH_2)_7$—; $R^3$ is hydrogen or $C_1$-$C_7$ alkyl; and n, which is the average number of oxyalkylene units, has a value within the range of 1 to 100; and
   wherein when $R^3$ is $C_1$-$C_7$ alkyl, the acid or ester derivative reactant has at least 1 mole % of trans-$\Delta^9$ unsaturation; or (b) a derivative made by sulfonating or sulfitating the alkoxylated fatty ester composition.

4. A water-soluble herbicide composition comprising:
(a) an alkoxylated fatty ester composition comprising a reaction product of a metathesis-derived $C_{10}$-$C_{17}$ monounsaturated acid, octadecene-1,18-dioic acid, or their ester derivatives with: (a) one or more alkylene oxides in the presence of an insertion catalyst to give an alkoxylated fatty ester; (b) a glycol ether or a glycol ether alkoxylate, optionally in the presence of an esterification or transesterification catalyst, to give an alkoxylated fatty ester; or (c) one or more alkylene oxides to give a fatty acid alkoxylate, followed by etherification of the fatty acid alkoxylate;
wherein the alkoxylated fatty ester composition has the formula:

$$R^2\text{—CO—O—}(AO)_n\text{—}R^1$$

wherein: $R^1$ is $C_1$-$C_4$ alkyl; AO is $C_2$-$C_4$ oxyalkylene; $R^2$ is $R^3$—CH=CH—$(CH_2)_7$— or $R^1(AO)_nO$—CO—$(CH_2)_7$—CH=CH—$(CH_2)_7$—; $R^3$ is hydrogen or $C_1$-$C_7$ alkyl; and n, which is the average number of oxyalkylene units, has a value within the range of 1 to 100; and
  wherein when $R^3$ is $C_1$-$C_7$ alkyl, the acid or ester derivative reactant has at least 1 mole % of trans-$\Delta^9$ unsaturation; or
  (b) a derivative made by sulfonating or sulfitating the alkoxylated fatty ester composition.

5. An antimicrobial composition comprising:
(a) an alkoxylated fatty ester composition comprising a reaction product of a metathesis-derived $C_{10}$-$C_{17}$ monounsaturated acid, octadecene-1,18-dioic acid, or their ester derivatives with: (a) one or more alkylene oxides in the presence of an insertion catalyst to give an alkoxylated fatty ester; (b) a glycol ether or a glycol ether alkoxylate, optionally in the presence of an esterification or transesterification catalyst, to give an alkoxylated fatty ester; or (c) one or more alkylene oxides to give a fatty acid alkoxylate, followed by etherification of the fatty acid alkoxylate;
wherein the alkoxylated fatty ester composition has the formula:

$$R^2\text{—CO—O—}(AO)_n\text{—}R^1$$

wherein: $R^1$ is $C_1$-$C_4$ alkyl; AO is $C_2$-$C_4$ oxyalkylene; $R^2$ is $R^3$—CH=CH—$(CH_2)_7$— or $R^1(AO)_nO$—CO—$(CH_2)_7$—CH=CH—$(CH_2)_7$—; $R^3$ is hydrogen or $C_1$-$C_7$ alkyl; and n, which is the average number of oxyalkylene units, has a value within the range of 1 to 100; and
  wherein when $R^3$ is $C_1$-$C_7$ alkyl, the acid or ester derivative reactant has at least 1 mole % of trans-$\Delta^9$ unsaturation; or
  (b) a derivative made by sulfonating or sulfitating the alkoxylated fatty ester composition.

* * * * *